United States Patent [19]

Fujimoto et al.

[11] 4,062,862
[45] Dec. 13, 1977

[54] 5-BENZYL-2-OXAZOLIDONE DERIVATIVES AND A PROCESS FOR PRODUCING THE SAME

[75] Inventors: Yasuo Fujimoto; Terumi Tamada, both of Tokyo, Japan

[73] Assignee: Nippon Chemiphar Co., Ltd., Tokyo, Japan

[21] Appl. No.: 701,506

[22] Filed: July 1, 1976

[30] Foreign Application Priority Data

July 4, 1975 Japan .............................. 50-082546
Oct. 17, 1975 Japan .............................. 50-125143

[51] Int. Cl.² .................. C07D 263/20; C07D 263/22; C07D 263/24
[52] U.S. Cl. .................. 260/307 C; 544/221; 560/30; 260/348.57; 260/348.49; 260/348.58; 424/272
[58] Field of Search .................. 260/307 C, 75 E

[56] References Cited

U.S. PATENT DOCUMENTS 3,020,262 2/1962 Speranza .............................. 260/47
3,133,932 5/1964 Horn et al. .............................. 260/307

OTHER PUBLICATIONS

Hassner et al., J. Org. Chem., vol. 39, No. 4, pp. 553–554 (1974).
Weiner, C.A. 55, 24709h (1961).

*Primary Examiner*—Raymond V. Rush
*Attorney, Agent, or Firm*—Oblon, Fisher, Spivak, McClelland & Maier

[57] ABSTRACT

5-Benzyl-2-oxazolidone derivatives of the formula:

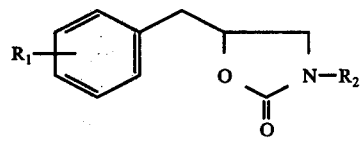

wherein $R_1$ represents a hydrogen, halogen, lower alkyl, trihalogenomethyl, phenyl, benzyl, hydroxy, lower alkoxy, phenoxy, benzyloxy, acyloxy, allyloxy, alkylcarbonyl, arylcarbonyl or alkylenedioxy group, and $R_2$ represents a hydrogen atom, a lower alkyl, lower alkylcarbonyl, lower-dialkylamino-lower-alkyl, aryl, aralkyl or arylcarbonyl group.

9 Claims, No Drawings

5-BENZYL-2-OXAZOLIDONE DERIVATIVES AND A PROCESS FOR PRODUCING THE SAME

BACKGROUND OF THE INVENTION

1. Field of the Invention

This invention relates to novel 5-benzyl-2-oxazolidone derivatives and to a process for producing the same.

The present inventors synthesized a wide variety of 5-benzyl-2-oxazolidone derivatives, examined their pharmacological effects and, as a result, found that 5-benzyl-2-oxazolidone derivatives of the following formula (I) possess an extremely excellent muscular relaxing activity:

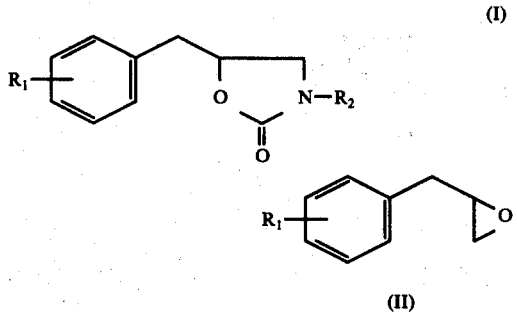

wherein $R_1$ represents a hydrogen or halogen atom, or a lower alkyl, trihalogenomethyl, phenyl, benzyl, hydroxy, lower alkoxy, phenoxy, benzyloxy, acyloxy, allyloxy, alkylcarbonyl, arylcarbonyl or alkylenedioxy group, and $R_2$ represents a hydrogen atom, a lower alkyl, lower alkylcarbonyl, lower-dialkylamino-lower alkyl, aryl, aralkyl or arylcarbonyl group.

2 Description of the Prior Art

The treatment of muscle tone diseases stands generally in need of both muscular relaxation and pain elimination. The muscle relaxants have been often used in combination with analgetics in clinical applications. Drugs which possess both analgesic and muscle relaxing properties have been expected to be prepared.

The 5-benzyl-2-oxazolidone derivatives represented by the formula (I) have an analgetic and antiinflammatory action together with a muscle relaxing action and are useful in the treatment of muscle tone and pain or inflammation accompanied by muscle tone. Also, the present compounds may be used in rehabilitation of muscle tone in patients with cerebral apoplexy.

SUMMARY OF THE INVENTION

It is, therefore, one object of this invention to provide novel 5-benzyl-2-oxazolidone derivatives represented by the formula (I).

It is another object of this invention to provide 5-benzyl-2-oxazolidone derivatives of the formula (I) which exert a strong muscular relaxing action together with an analgetic and antiinflammatory action.

It is a further object of this invention to provide a novel process for producing 5-benzyl-2-oxazolidone derivatives of the formula (I).

In the desired compounds of the formula (I), $R_1$ may be substituted at 2-, 3- or 4-position of the benzene ring, preferably including, for example, halogen atoms such as chlorine, fluorine or bromine, lower alkyl groups such as methyl, ethyl, straight or branched propyl or butyl; lower alkoxy groups such as methoxy, ethoxy, propoxy or butoxy; and alkylenedioxy groups such as 3,4-methylenedioxy and a phenoxy group.

$R_2$ includes a hydrogen atom; lower alkyl groups such as methyl, ethyl, propyl or butyl; lower alkylcarbonyl groups such as acetyl, propionyl or butylyl; lower-dialkylamino-lower-alkyl groups such as dimethylaminomethyl, dimethylaminoethyl, dimethylaminopropyl, diethylaminoethyl or diethylaminopropyl; aryl groups such as phenyl or naphthyl; aralkyl groups such as benzyl; and arylcarbonyl groups such as benzoyl or naphthoyl. The aryl groups mentioned above may be substituted by halogen atoms.

The term "lower" alkyl or "lower" alkoxy used throughout this specification means that having 1 to 5 carbon atoms.

According to the present invention, 5-benzyl-2-oxazolidone derivatives of the formula (I) are produced by reacting allylbenzene oxides of the formula (II) with N-substituted)-carbamates of the formula (III) according to the following process (a):

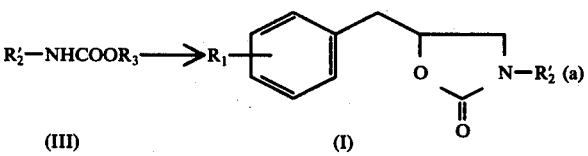

wherein $R_2'$ represents a hydrogen atom, or a lower alkyl, lower-dialkylamino-lower-alkyl, aryl or aralkyl group, $R_3$ represents the ester residue and $R_1$ is the same as defined above.

Allylbenzene oxide derivatives of the formula (II) to be used as starting materials in the inventive process may be, for example, easily preppared by reacting allylbenzene derivatives of the formula IIV) with paracids according to the following process (b):

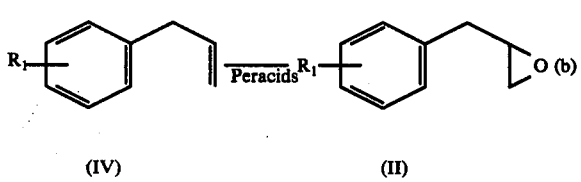

wherein $R_1$ is the same as defined above.

In conducting the process (b), the compound of the formula (IV) may be reacted with peracids such as perbenzoic acid, m-chloroperbenzoic acid, peracetic acid and trifluoroperacetic acid, or halohydrin and alkaline agents. The reaction is carried out in the solvent which does not participate in reaction such as chloroform, benzene and toluene at 0° C to room temperature, preferably at 0° – 5° C. After the completion of the reaction, the compound of the formula (II) may be isolated from the reaction mixture by usual methods. For example, an organic acid to be separated from the mixture is filtered off, the filtrate is washed with sodium hydroxide solution, then water, and dried. The solvent is evaporated to obtain the residue, which is distilled under reduced pressure to give the compound of the formula (II).

In conducting the process (a), allylbenzene oxide derivatives of the formula (II) are molten or heated with stirring with an (N-substituted)-carbamate of the formula (III) in the presence of a catalyst.

Preferable catalysts to be used in the present process, include alkaline agents such as trimethylamine, triethylamine, quaternary ammonium halide, n-butoxy lithium, sodium hydroxide or lithium hydroxide; and Lewis acids such as, zinc bromide, zinc chloride, iron chloride or lithium chloride. The reaction is preferably conducted at 100° to 150° C for several hours.

Alternatively, 5-benzyl-2-oxazolidone derivatives of the formula (I), wherein $R_2$ represents substituents other than hydrogen atom, can also be produced according to the following process (c) by reacting 5-benzyl-2-oxazolidone derivatives of the formula (V) obtained according to the process (a) wherein $R_2$ represents a hydrogen atom with halides of the formula (VI):

wherein R'' represents a lower alkyl, lower alkylcarbonyl, lower-dialkylamino-lower-alkyl, aryl, aralkyl or arylcarbonyl, X represents a halogen atom and $R_1$ is the same as defined above.

In conducting the process (c), the compound of the formula (V) is reacted by application of heat, with the compound of the formula (VI) in the inert solvent such as methanol, ethanol and benzene in the presence of alkaline agents such as potassium hydroxide, sodium hydroxide and metallic sodium.

A list of methods suitable for preparing the present compounds is given below. In these methods, R is a non-substituted or substituted benzyl group.

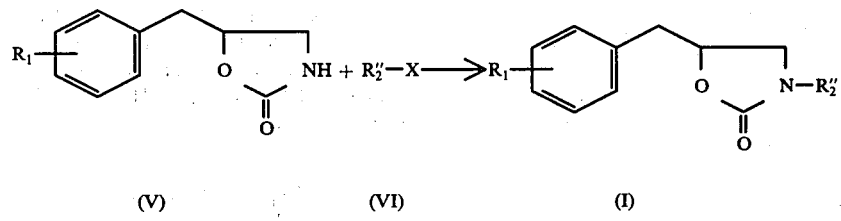

(V)    (VI)    (I)

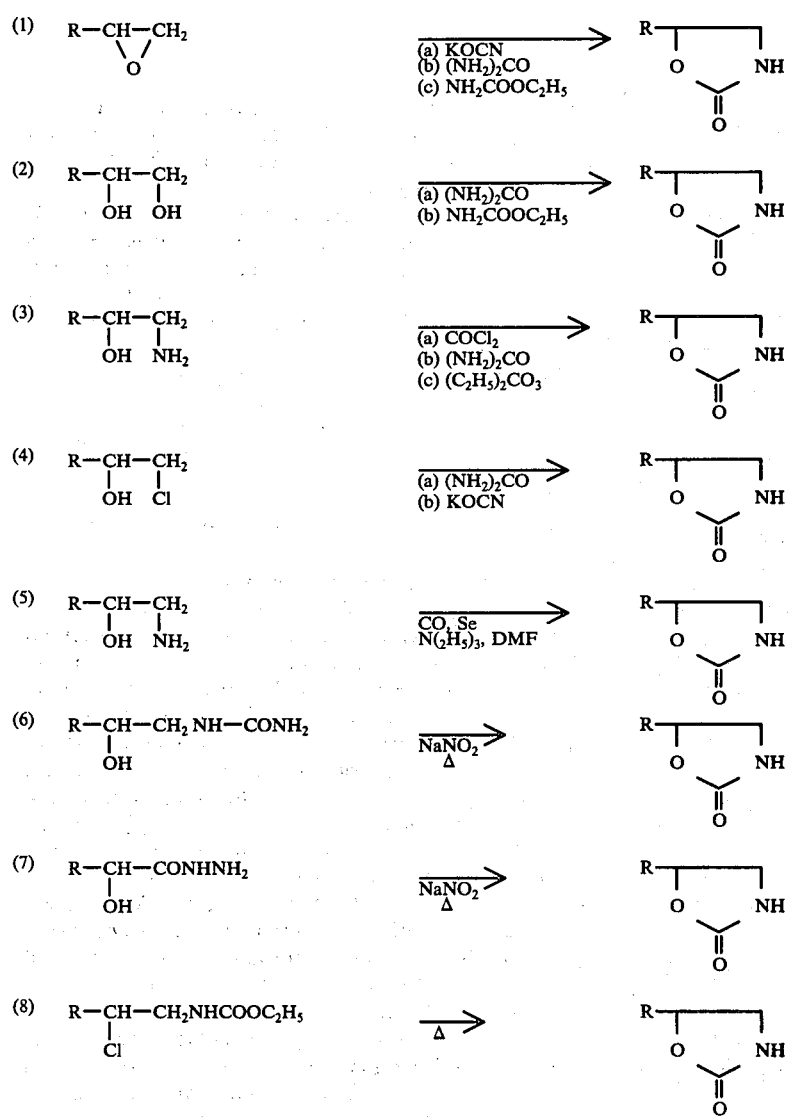

(9) 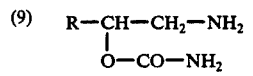  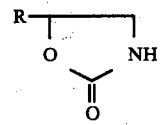

-continued

(10) 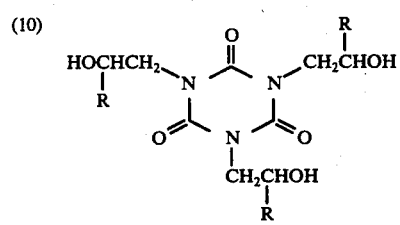  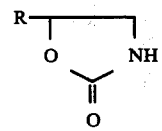

The compounds of the formula (I) of the present invention possess excellent muscular relaxing, analgetic and antiinflammatory actions.

The effects of typical compounds of the present are illustrated below.

1. Muscular relaxing effect dd Male mice weighing 18 to 22 g, one group consisting of 10 animals, were orally given the compounds (I) to (V) as indicated below suspended in 0.2% carboxymethylcellulose solution in a dose of 0.25ml/10g-body weight. Mephenesin was used as active placebo. The experiment was conducted according to the methods (a) to (e) as described below and $ED_{50}$ values were calculated by the Litchfield Wilcoxon method, based on the maximum response at each dose which was measured at 15, 30, 45, 60, 90, 120, 150 and 180 minutes after the administration of the compounds.

a Rotarod Method:

Mice were placed on Rotar Load (made by Natsume Seisakusho Co., Ltd.) having a diameter of 3 cm rotating at a speed of 10 rpm and falling (occurring within 3 minutes) was observed.

b. Traction Test:

A wire having a diameter of 1mm was grasped by the front legs of mice and the mice were observed to see whether mice hung their hind legs on said wire by chinning themselves up within 5 seconds.

c. Inclined Plane Test:

Mice were placed on veneer inclined at an angle of 30° and on wire-netting inclined at an angle of 60° of which one division is 5 mm square, and mice sliding down were observed as positive, in comparison with normal behavior.

d. Righting Reflex Test:

Mice which turned their faces upward and had a disappearance of righting reflex after 30 minutes were referred to as positive.

e. Pinna Reflex Test:

Pinna reflex was observed by using mandolin wire for ¼ injection syringe.

f. Corneal Reflex Test:

Corneal reflex was observed by using mandolin wire for ¼ injection syringe.

The results obtained were shown in Table 1 and Table 2.

Table 1

$ED_{50}$ values (mg/kg) of the present compounds and mephenesin in mice

| Compounds | Methods | R.R | T.T | I.P | R.r | P.r | C.r |
|---|---|---|---|---|---|---|---|
| Compound | I | 460 | 660 | 940 | 1100 | 800 | — |
| Compound | II | 340 | 500 | 500 | 810 | 520 | 1100 |
| Compound | III | 175 | 350 | 380 | 500 | 380 | 500 |
| Compound | IV | 210 | 390 | 330 | 660 | <500 | 560 |
| Compound | V | 240 | 380 | 520 | 750 | 530 | 750 |
| Mephenesin | | 268 | 460 | 470 | 640 | 420 | 680 |

| Compound | I : 5-benzyl-2-oxazolidone |
| Compound | II : 5-benzyl-3-methyl-2-oxazolidone |
| Compound | III : 5-(o-methoxybenzyl)-2-oxazolidone |
| Compound | IV : 5-(o-chlorobenzyl)-2-oxazolidone |
| Compound | V : 5-(p-chlorobenzyl)-2-oxazolidone |

Table 2

Inhibition percent of the central muscular relaxing effect of the present compounds and mephenesin in mice.

| Test compounds | | Dose (mg/kg) | R.R | T.T | I.P | R.r | P.r | C.r |
|---|---|---|---|---|---|---|---|---|
| Compound | VI | 500 | 60 | 40 | 50 | 10 | 10 | 0 |
| Compound | VII | 500 | 80 | 40 | 40 | 0 | 0 | 0 |
| Compound | VIII | 500 | 90 | 40 | 40 | 10 | 10 | 0 |
| Compound | IX | 500 | 90 | 60 | 60 | 0 | 60 | 0 |
| Compound | X | 500 | 80 | 40 | 40 | 30 | 40 | 0 |
| Compound | XI | 500 | 100 | 90 | 80 | 10 | 60 | 0 |
| Compound | XII | 500 | 100 | 60 | 80 | 0 | 20 | 0 |
| Compound | XIII | 500 | 90 | 70 | 50 | 20 | 0 | 10 |
| GP | | 500 | 60 | 40 | 30 | 0 | 10 | 0 |
| mephenesin | | 500 | 80 | 40 | 60 | 20 | 20 | 0 |

| Compound | VI : 5-(o-ethylbenzyl)-2-oxazolidone |

Table 2-continued

Inhibition percent of the central muscular relaxing effect of the present compounds and mephenesin in mice.

| Test compounds | Dose (mg/kg) | R.R | T.T | I.P | R.r | P.r | C.r |
|---|---|---|---|---|---|---|---|
| Compound VII | : 5-(p-ethylbenzyl)-2-oxazolidone | | | | | | |
| Compound VIII | : 5-(o-trifluoromethylbenzyl)-2-oxazolidone | | | | | | |
| Compound IX | : 5-(m-trifluoromethylbenzyl)-2-oxazolidone | | | | | | |
| Compound X | : 5-(o-allyloxybenzyl)-2-oxazolidone | | | | | | |
| Compound XI | : 5-(p-fluorobenzyl)-2-oxazolidone | | | | | | |
| Compound XII | : 5-(o-bromobenzyl)-2-oxazolidone | | | | | | |
| Compound XIII | : 5-(o-fluorobenzyl)-2-oxazolidone | | | | | | |
| GP | : γ-phenylpropylcarbamate | | | | | | |
| R.R | : Rotarod Method | | | | | | |
| T.T | : Traction Test | | | | | | |
| I.P | : Inclined Plane Test | | | | | | |
| R.r | : Righting Reflex Test | | | | | | |
| P.r | : Pinna Reflex Test | | | | | | |
| C.r | : Corneal Reflex Test | | | | | | |

2. Analgetic effect a. Acetic Acid-Induced Writhing Method dd Male mice weighing 18 to 22g, one group consisting of 10 animals, were given the intraperitoneal injection of 0.6% acetic acid in a dose of 0.1ml/10g-body weight. The number of writhing syndromes occurring within 20 minutes after injection was observed. Animals were orally given the test compounds suspended in 0.2% carboxymethylcellulose solution 30 minutes before the injection of acetic acid in a dose of 100mg/kg-body weight. Inhibitory percent was estimated in comparison with a control given the 0.2% carboxymethycellulose solution only. Aminopyrine was used as active placebo.

The results obtained were shown in Table 3.

Table 3

Analgetic effects of the present compounds and aminopyrine on acetic acid-induced writhing syndrome in mice

| Compounds | | Dose (mg/kg) | Numbers of animals | Writhing syndrome | Inhibitory per cent |
|---|---|---|---|---|---|
| Control | | 0.2% CMC | 50 | 52.1 ± 2.7 | — |
| Compound | I | 100 | 10 | 42.3 ± 5.9 | 18.9 |
| Compound | II | 100 | 10 | 45.9 ± 4.8 | 11.9 |
| Compound | III | 100 | 10 | 39.1 ± 6.4 | 24.9 |
| Compound | IV | 100 | 10 | 12.8 ± 3.6 | 75.4 |
| Compound | V | 100 | 10 | 45.5 ± 5.3 | 12.8 |
| Aminopyrine | | 100 | 10 | 19.3 ± 6.0 | 62.9 |

Compounds I to V are the same as defined in Table 1.

b. Pressure Test dd Male mice weighing 18 to 22 g (pain threshold ranging within 30 to 50 mmHg), one group consisting of 10 animals, were given orally the test compounds suspended in 0.2% carboxymethylcellulose solution in a dose of 100mg/kg-body weight. Pain threshold were measured at 30, 60, 90 and 120 minutes after the administration of the test compounds while pain reaction occurring by application of pressure on tails of animals was referred to as indication. Aminopyrine was used as active placebo.

The results obtained were shown in Table 4.

Table 4

Effects of the present compounds and aminopyrine on the pain threshold in mice

| Compound | | Dose (mg/kg) | Numbers of animals | Pain threshold (mmHg) Mean ± SE | | | | | Increase Ratio |
|---|---|---|---|---|---|---|---|---|---|
| | | | | Placebo | 30 min | 60 min | 90 min | 120 min | |
| Compound | I | 100 | 10 | 43.4 ± 1.7 | 58.2 ± 3.2** | 57.8 ± 3.2** | 51.5 ± 2.8 | 50.7 ± 2.2 | 1.34 |
| Compound | II | 100 | 10 | 36.1 ± 2.3 | 49.1 ± 4.5* | 49.2 ± 3.3** | 43.5 ± 4.7 | 36.3 ± 3.9 | 1.36 |
| Compound | III | 100 | 10 | 38.7 ± 2.2 | 43.7 ± 4.9 | 46.5 ± 4.2 | 42.9 ± 3.1 | 39.2 ± 3.6 | 1.20 |
| Compound | IV | 100 | 10 | 35.0 ± 2.2 | 69.8 ± 4.5*** | 56.7 ± 5.3** | 53.3 ± 5.5* | 51.8 ± 6.2* | 1.89 |
| Compound | V | 100 | 10 | 47.3 ± 2.8 | 54.6 ± 4.9 | 51.3 ± 4.3 | 48.8 ± 2.7 | 48.2 ± 1.7 | 1.15 |
| Compound | VIII | 100 | 10 | 48.3 ± 1.9 | 62.0 ± 4.6* | 60.2 ± 3.0** | 57.5 ± 3.2* | 52.9 ± 2.0 | 1.28 |
| Compound | XII | 100 | 10 | 48.0 ± 1.8 | 59.6 ± 3.4*** | 59.4 ± 3.7** | 57.5 ± 1.9*** | 52.7 ± 2.1 | 1.24 |
| Compound | XIII | 100 | 10 | 47.6 ± 1.6 | 52.1 ± 3.4 | 53.7 ± 2.6 | 50.4 ± 2.8 | 47.3 ± 1.8 | 1.13 |
| Aminopyrine | | 100 | 10 | 34.4 ± 2.5 | 75.7 ± 5.4*** | 67.3 ± 5.4*** | 70.8 ± 5.3*** | 53.1 ± 4.5*** | 2.20 |

*p <0.05, p <0.01, *p <0.001
Compounds I to V and Compounds VIII, XII, XIII are the same as defined in Table I and Table II.

3. Antiinflammatory effect on carrageenan-induced edema

Wistar male rats weighing 170 to 190 g which fasted for 24 hours, one group consisting of 6 to 7 animals, were orally given the test compounds suspended in 0.2% carboxymethylcellulose solution in a dose of 200 mg/kg-body weight. One hour after the administration of the test compounds, the hind paw was given a subcutaneous injection of 0.05ml of 0.5% carrageenan saline solution, and volume of the hind paw was measured at 1, 2, 3, 4, 5 and 6 hours after the injection of carrageenan by a volume differential meter. Inhibitory percent was calculated based on the swelling in the control. Phenybutazone was used as active placebo.

The results obtained are shown in Table 5 and Table 6.

Table 5

Effects of the present compounds and phenylbutazone on carrageenan-induced edema in rats

| Compounds | Dose (mg/kg) | Numbers of animals | Inhibitory (per cent) 3 hrs. | 6 hrs. |
|---|---|---|---|---|
| Compound I | 200 | 7 | 49.5 | 13.0 |
| Compound II | 200 | 7 | 33.3 | 19.7 |
| Compound III | 200 | 6 | 32.7 | 23.3 |
| Compound IV | 200 | 6 | 16.8 | 15.9 |
| Compound V | 200 | 7 | 30.6 | 22.8 |
| Phenylbutazone | 200 | 7 | 76.6 | 45.1 |

Compunds I to V are the same as defined in Table 1.

Table 6

Effects of the present compounds and phenylbutazone on carrageenan-induced edema in rats

| Test compounds | Dose (mg/kg) | Numbers of animals | Inhibitory per cent 1 hr | 2 hrs. | 3 hrs. | 4 hrs. | 5 hrs. | 6 hrs. |
|---|---|---|---|---|---|---|---|---|
| Compound VI | 100 | 6 | 27.8 | 36.3*** | 53.6*** | 28.9*** | 22.0* | 17.4 |
| Compound VIII | 200 | 3 | 21.7 | 49.7*** | 27.4* | 35.6* | 9.2 | 0.5 |
| Compound IX | 200 | 3 | 45.0 | 49.4** | 20.8 | 11.3 | 14.5 | 11.5 |
| Compound XI | 200 | 3 | 38.3 | 47.5** | 44.5** | 34.4* | 9.2 | 8.9 |
| Compound XIV | 100 | 5 | 12.9 | 35.2* | 40.0** | 15.6 | 9.1 | — |
| Compound XV | 100 | 6 | 59.5** | 57.1*** | 59.9*** | 30.8** | 26.1* | 23.2* |
| Phenylbutazone | 100 | 6 | 59.1** | 54.6*** | 59.7*** | 68.2*** | 63.4*** | 52.6*** |

Marks *,  and * are the same defined in Table 4.
Compound VI, VIII, IX and XI are the same as defined in Table 2.
Compound XIV: 5-(o-phenylbenzyl)-2-oxazolidone
Compound XV: 5-(o-phenoxybenzyl)-2-oxazolidone 4. Acute toxicity dd Male mice weighing 18 to 22 g, one group consisting of 5 animals, were orally given the test compounds suspended in 0.2% carboxymethylcellulose solution and, as a result, acute toxicity of the present compounds (LD50) was found to be within 700 - 900 mg/kg.

The invention is illustrated below in further detail with reference to Examples, but the invention is not limited to the Examples.

EXAMPLE 1

5-benzyl-2-oxazolidone:

a. 21.6 g of allylbenzene was dissolved in 200 ml of chloroform and to the mixture was added dropwise 41.4 g of m-chloroperbenzoic acid dissolved in 1l of chloroform at 0° - 5° C. The resulting mixture was reacted with slow stirring for 55 hours while maintaining the temperature at 0° - 5° C. After the completion of the reaction, m-chlorobenzoic acid crystals were filtered off and the filtrate was washed twice with 5% sodium hydroxide solution and then water. After dried over anhydrous sodium sulfate, the solvent was evaporated to obtain the residue. This was distilled under reduced pressure to give 16.9 g (yield 70.5%) of allylbenzene oxide as colourless oil having a boiling point of 60° C/2 mmHg.

b. The mixture of 1.34 g of allylbenzene oxide, 4.5 g of ethyl carbamate and 100 mg of triethylamine was molten at 130° - 140° C for 2 hours. After the reaction, the mixture was dissolved in chloroform and washed with water. After drying over anhydrous sodium sulfate, the solvent was evaporated to obtain the pale yellow oily substance. This was recrystallized from n-hexane, and then water to give 1.15 g (yield 65.0%) of 5-benzyl-2-oxazolidone as scaly crystals.

Elemental Analysis: as $C_{10}H_{11}NO_2$. Calculated (%) : C: 67.78; H: 6.26; N: 7.91; Found (%) : C: 67.82; H: 6.44; N: 7.76.

IR $(v_{max}^{CHCl_3}$ cm$^{-1})$ : 3740, 3280 (OH, NH), 1765 (OCOHN).

NMR (CDCl$_3$) δ : 3.03 (2H, m, Ar—CH$_2$—). 3.22-3.64 (2H, m, N—CH$_2$—) 4.83 (1H, q, —CH$_2$CHCH$_2$—) 6.25 (1H, broad S, —NHCOO—) 7.28 (5H, S, C6H5).

MS(m/e) : 177 (M+).

EXAMPLE 2

5-benzyl-3-phenyl-2-oxazolidone:

The mixture of 1.0 g of alylbenzene oxide, 5 g of ethyl N-phenylcarbamate and 100 mg of triethylamine was molten at 130° - 140° C for 2 hours. After cooling, a small quantity of ethanol was added to the mixture to separate white powder, which was filtered to obtain 1.2 g (yield 64.6%) of product. This was recrystallized from ethanol to give 5-benzyl-3-phenyl-2-oxazolidone as scaly crystals having a melting point of 90° C.

Elemental Analysis: as $C_{16}H_{15}NO_2$. Calculated (%) : C: 75.87; H: 5.97; N: 5.53; Found (%) : C: 75.74; H: 5.99; N: 5.41.

IR $(v_{max}^{CHCl_3}$ cm$^{-1}$: 1765 (OCONH), 1610 (N—Ar).
NMR (CDCl$_3$) δ : 3.09 (2H, m, Ar—CH$_2$) 3.61 - 4.04 (2H, m, N—CH$_2$) 4.85 (1H, m, —CH$_2$CHCH$_2$—) 7.20 - 7.53 (5H, m, N—C$_6$H$_5$) 7.30 (5H, S. C$_6$H$_5$)

MS (m/e) : 253 (M+).

EXAMPLE 3

3-m-fluorophenyl-5-benzyl-2-oxazolidone:

a. The mixture of 150 ml of methanol, 25 g of m-fluoroaniline, 30 g of triethylamine and 32.5 g of ethyl chlorocarbamate was heated under reflux condition. After the completion of the reaction, the solvent was evaporated under reduced pressure to obtain the residue, to which was added 100 ml of water and 100 ml of benzene. The benzene layer was separated, washed twice with water and dried over anhydrous sodium sulfate. The solvent was evaporated to obtain the residue, which was distilled under reduced pressure, and there was obtained 12.5 g (yield 34.8%) of ethyl m-fluorophenylcarbamate as colourless oil having a boiling point of 102° C/1.5 mmHg.

IR ($\nu_{max}^{CHCl_3}$ cm$_{-1}$) : 3430 (NH), 1730 (CO).

NMR (CDCl$_3$) δ : 1.26 (3H, t, —CH$_2$CH$_3$); 4.18 (2H, q, —CH$_2$CH$_3$); 6.60 - 7.36 (4H, m, C$_6$H$_4$).

b. The mixture of 1.8 g of allylbenzene oxide, 3.6 g of ethyl m-fluorophenylcarbamate and 100 mg of triethylamine was heated with stirring at 130° - 140° C for 2 hours. After cooling, to the mixture was added a small quantity of ethanol to separate the white powder which was collected by filtration. This was recrystallized from ethanol, there was obtained 1.55 g (yield 42.7%) of 3-m-fluorophenyl-5-benzyl-2-oxazolidone as colourless needles having a melting point of 96° - 97.5° C.

Elemental Analysis: as C$_{16}$H$_{14}$NO$_2$F. Calculated (%): C: 70.9; H: 5.17; N: 5.17. Found (%): C: 70.76; H: 5.18; N: 5.02.

IR ($\nu_{max}^{CHC_3}$ cm$^{-1}$) : 1760 (OCON).

NMR (CDCl$_3$) δ : 3.02 (2H, m, Ar-CH$_2$); 3.52 - 3.94 (2H, m, CONCH$_2$—); 4.78 (1H, m, CH$_2$CHCH$_2$—Ar); 6.62 - 7.32 (4H, m, C$_6$H$_4$); 7.20 (5H, S, C$_6$H$_5$).

MS (m/e) : 271 (M+).

EXAMPLE 4

5-benzyl-3-methyl-2-oxazolidone:

500 mg of metallic sodium was dissolved in 50 ml of anhydrous methanol and to the mixture was added 3.5 g of 5-benzyl-2-oxazolidone. The thus obtained mixture was heated under reflux condition for 18 hours. After the completion of the reaction, the solvent was distilled off to obtain the residue, which was suspended in 30 ml of anhydrous benzene. To the suspension was added 11.2 g of methyl iodide. The resulting mixture was heated under reflux condition for 16 hours, and then filtered. The filtrate obtained was distilled off under reduced pressure to obtain the residue, which was chromatographed over silica gel; and eluted with the mixed solvent of benzene and acetone (100:3). There was obtained 3.2 g (yield 84.3%) of crude produce. This was recrystallized from n-hexane to give 5-benzyl-3-methyl-2-oxazolidone as colourless needles having a melting point of 80° - 82° C.

Elemental Analysis: as C$_{11}$H$_{13}$NO$_2$. Calculated (%): C: 69.09; H: 7.33; N: 6.85; Found (%): C: 69.32; H: 7.39; N: 6.87.

IR ($\nu_{max}^{CHCl_3}$ cm$^{-1}$) : 1750 (OCON), disappearance of NH absorption.

NMR (CDCl$_3$) δ : 2.68 (3H, S, N—CH$_3$); 2.88 (2H, m, Ar—CH$_2$); 3.04 - 3.50 (2H, m, N—CH$_2$); 4.56 (1H, m, —CH$_2$CHCH$_2$—); 7.12 (5H, S, C$_6$H$_5$).

MS (m/e) : 191 (M+).

EXAMPLE 5

5-benzyl-3-acetyl-2-oxazolidone:

500 mg of metallic sodium was dissolved in 100 ml of anhydrous benzene and to the mixture was added 3.5 g of 5-benzyl-2-oxazolidone. The thus obtained mixture was heated under reflux condition for 20 hours. After cooling to room temperature, was 4.7 g of acetyl chloride was added dropwise to the mixture and the resulting mixture was refluxed for another 7 hours. After the completion of the reaction, the mixture was filtered and the filtrate was distilled off under reduced pressure to obtain the residue, which was chromatographed over silica gel, and eluted with the mixed solvent of benzene and acetone (100:3). There was obtained 3.1 g (yield 73.8%) of crude product. This was recrystallized from benzene-n-hexane to give 5-benzyl-3-acetyl-2-oxazolidone as colourless needles having a melting point of 90° C.

Elemental Analysis: as C$_{12}$H$_{13}$NO$_3$. Calculated (%): C: 65.73; H: 5.93; N: 6.43; Found (%): C: 65.88; H: 6.16; N: 6.43.

IR ($\nu_{max}^{CHCl_3}$ cm$^{-1}$) : 1785 (OCON), 1700 (CH$_3$CO).

NMR (CDCl$_3$) δ : 2.40 (1H, S. NCOCH$_3$); 3.01 (2H, q, Ar—CH$_2$); 3.56 - 4.03 (2H, m, —CH$_2$—N); 4.76 (1H, m, —CH$_2$CHCH$_2$—); 7.23 (5H, S, C$_6$H$_5$).

MS (m/e) : 219 (M+).

EXAMPLE 6

5-benzyl-3-n-propyl-2-oxazolidone:

700 mg of metallic sodium was dissolved in 50 ml of anhydrous methanol and to the mixture was added 5.3 g of 5-benzyl-2-oxazolidone. The solvent was evaporated under reduced pressure to obtain the residue, in which was suspended 300 ml of anhydous benzene and heated with stirring for 20 hours. Then, to the mixture was added 25 g of n-propyl iodide and the resulting mixture was heated under reflux condition for another 16 hours. After the completion of the reaction, the mixture was filtered to collect the filtrate. The solvent was evaporated under reduced pressure to obtain the residue, which was distilled under reduced pressure to give 3.9 g (yield 59.3%) of 5-benzyl-3-n-propyl-2-oxazolidone as colourless oil having a boiling point of 169° - 172° C/2 mmHg.

Elemental Analysis: as C$_{13}$H$_{17}$NO$_2$. Calculated (%): C: 71.20; H: 7.82; N: 6.39. Found (%): C: 70.72; H: 7.86; N: 6.39.

IR ($\nu_{max}^{CHCl_3}$ cm$^{-1}$) : 2800, 2925 (—CH$_2$), 2950 (CH$_3$), 1745 (OCON).

NMR (CDCl$_3$) δ : 0.84 (3H, t, C$\underline{H}_3$); 1.46 (2H, m, —C$\underline{H}_2$CH$_3$); 2.80 - 3.56 (6H, m,

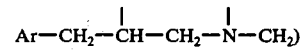

4.68 (1H, m, Ar—CH$_2$—C$\underline{H}$); 7.22 (5H, S. C$_6\underline{H}_5$).

MS (m/e) : 219 (M+).

EXAMPLE 7

5-benzyl-3-benzyl-2-oxazolidone:

300 mg of metallic sodium was dissolved in 30 ml of anhydrous methanol and to the mixture was added 1.8 g of 5-benzyl-2-oxazolidone. The solvent was evaporated under reduced pressure to obtain the residue, in which was suspended 40 ml of anhydrous benzene. The suspension thus obtained was heated under reflux condition for 16 hours. Then the mixture was refluxed for another 19 hours. After the completion of the reaction, the mixture was filtered to collect the filtrate, which was distilled under reduced pressure to obtain the residue. This residue was solidified by washing several times with n-hexane and there was obtained 2.2 g (yield 82.5%) of white powder. This was recrystallized from isopropanol to give 5-benzyl-3-benzyl-2-oxazolidone as colourless prismatic crystals having a melting point of 81° – 82° C.

Elemental Analysis: as $C_{17}H_{17}NO_2$. Calculated (%): C: 76.50; H: 6.27; N: 5.10. Found (%): C: 76.38; H: 6.41; N: 5.24.

IR $(\nu_{max}^{CHCl_3}$ cm$^{-1})$: 2925 (—CH$_2$), 1760 (OCON).

NMR (CDCl$_3$) δ : 2.72 – 3.40 (6H, m,

Ar—CH$_2$—CH—CH$_2$—N—CH$_2$—)

4.16 (2H, S, Ar—CH$_2$—N—); 7.0 – 7.20 (5H, m, N—C$_6$H$_5$); 7.24 (5H, S, C$_6$H$_5$).

MS (m/e) : 267 (M+).

EXAMPLE 8

5-benzyl-3-benzoyl-2-oxazolidone:

700 mg of metallic sodium was dissolved in 100 ml of anhydrous methanol and to the mixture was added 5.3 g of 5-benzyl-2-oxazolidone. The solvent was evaporated under reduced pressure to obtain the residue, which was suspended in 150 ml of anhydrous benzene. The suspension thus obtained was heated under reflux condition for 24 hours. Then to the mixture was added 6.7 g of benzoyl chloride and the mixture was refluxed for another 18 hours. After the completion of the reaction, the mixture was filtered to collect the filtrate, which was washed with diluted sodium hydroxide solution, then with water and dried over anhydrous sodium sulfate. The solvent was evaporated, there was obtained 9.9 g (yield 88.3%) of 5-benzyl-3-benzoyl-2-oxazolidone as white powder. This was recrystallized from ethanol to give colourless needles having a melting point of 109° – 110.5° C.

Elemental Analysis: as $C_{17}H_{15}NO_3$. Calculated (%): C: 72.59; H: 5.34; N: 4.90. Found (%): C: 72.58; H: 5.37; N: 4.98.

IR $(\nu_{max}^{CHCl_3}$ cm$^{-1})$ : 1685 (NCOAr), 1790 (OCON).

NMR (CDCl$_3$) δ : 3.0 (2H, d, Ar—CH$_2$); 3.72 – 4.16 (2H, m, Ar—CH$_2$—CH—CH$_2$—N); 4.85 (1H, m, Ar—CH$_2$—CH—CH$_2$—); 7.32 (5H, S, COC$_6$H$_5$); 7.40 (5H, S, CH$_2$—C$_6$H$_5$).

MS (m/e) : 281 (M+).

EXAMPLE 9

5-benzyl-3-β(dimethylamino)ethyl-2-oxazolidone:

1.5 g of metallic sodium was dissolved in 50 ml of anhydrous methanol and to the mixture was added 5.3 g of 5-benzyl-2-oxazolidone. The solvent was evaporated under reduced pressure to obtain the residue, which was suspended in 100 ml anhydrous benzene. The suspension thus obtained was heated under reflux condition for 20 hours. Then to the mixture was added 4.8 g of β-dimethylaminoethyl chloride and the resulting mixture was refluxed for another 20 hours. After the completion of the reaction, the mixture was filtered to collect the filtrate. The solvent was evaporated under reduced pressure to obtain the residue. This residue was distilled under reduced pressure, there was obtained 4.0 g (yield 53.4%) of 5-benzyl-3- β(dimethylamino)-ethyl-2-oxazolidone as colourless oil having a boiling point of 176° C/1.5 mmHg. This product was hydroxchloride, which was recrystallized from ethanol-diethyl ether to give colourless needles having a melting point of 202° – 204° C.

Elemental Analysis: as $C_{14}H_{20}N_2O_2$ HCl. Calculated (%): C: 59.00; H: 7.02; N: 9.83. Found (%): C: 58.97; H: 7.44; N: 10.10.

IR $(\nu_{max}^{KBr}$ cm$^{-1})$ : as hydroxhloride : 2960 (N(CH$_3$)$_2$); 2450 – 2670;

1730 (OCON).

NMR (CDCl$_3$) δ : 2.20 (6H, S,

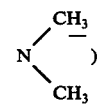

2.33 (2H, t,

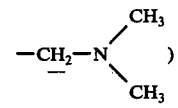

2.76 – 3.66 (6H, m, Ar—CH$_2$—CH—CH$_2$—N—CH$_2$—); 4.75 (1H, m, Ar—CH$_2$CHCH$_2$); 7.24 (5H, S, C$_6$H$_5$).

MS (m/e): 284 (M+).

EXAMPLE 10

5-benzyl-3-γ(dimethylamino)propyl-2-oxazolidone:

2.0 g of metallic sodium was dissolved in 100 ml of anhydrous methanol and to the mixture was added 7.1 g of 5-benzyl-2-oxazolidone. The solvent was evaporated under reduced pressure to obtain the residue, which was suspended in 150 ml of anhydrous benzene. The suspension was heated under reflux condition for 18 hours. Then to the mixture was added 6.95 g of γ-(dimethylamino)propyl chloride and the resulting mixture was refluxed for another 18 hours. After the completion of the reaction, the mixture was filtered to collect the filtrate. The solvent was evaporated under reduced pressure to obtain the residue. This residue was distilled under reduced pressure, there was obtained 6.4 g (yield 61%) of 5-benzyl-3-δ(dimethylamino)propyl-2-oxazolidone as colourless oil having a boiling point of 184° – 186° C/2 mmHg. This was picrate, which was recrystallized from ethanol to give yellow fine needles having a melting point of 136° – 138.5° C.

Elemental Analysis: as $C_{21}H_{25}N_5O_9$(picrate). Calculated (%): C: 51.32; H: 5.13; N: 14.25. Found (%): C: 51.11; H: 5.00; N: 14.50.

IR $(\nu_{max}^{CHCl_3}$ cm$^{-1})$ : 2950 (N—(CH$_3$)$_2$), 2860 (—CH$_2$)$_3$N), 1745 (OCON<).

NMR (CDCl$_3$) δ : 1.60 (2H, q, N—CH$_2$—CH$_2$—CH$_2$-N<); 2.16 (6H, S, —N (CH$_3$)$_2$); 2.12 – 2.27 (2H, m, N—CH$_2$CH$_2$CH$_2$N(CH$_3$)$_2$); 2.90 – 3.60 (6H, m,

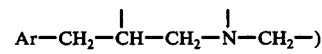

4.70 (1H, m, Ar—CH$_2$—CH—); 7.25 (5H, S, C$_6$H$_5$).

MS (m/e) : 262 (M+)

EXAMPLE 11

5-(3,4-methylenedioxybenzyl)-2-oxazolidone:

a. 16.2 g of safrole was dissolved in 100 ml of chloroform and to the mixture was added dropwise 20.7 g of m-chloroperbenzoic acid dissolved in 500 ml of chloroform at 0°-5° C. The resulting mixture was allowed to stand with slow stirring for 55 hours, while maintaining the temperature at 0° - 5° C. After the completion of the reaction, m-chlorobenzoic acid crystals were filtered and the filtrate was washed twice with 5% sodium hydroxide solution, and then with water. After drying over anhydrous sodium sulfate, the solvent was evaporated to obtain the residue. This was distilled under reduced pressure to give 7.0 g (yield 39.3%) of safrole oxide as colourless oily substance having a boiling point of 108° - 110° C/3 mmHg.

Elemental Analysis: as $C_{10}H_{10}O_3$. Calculated (%): C: 67.41; H: 5.62. Found (%): C: 66.95; H: 5.40.

b. The mixture of 890 mg of safrole oxide, 900 mg of ethyl carbamate and 100 mg of triethylamine was molten at 140° C for 2 hours. After the completion of the reaction, the mixture was dissolved in a small quantity of chloroform and washed with water. After drying over anhydrous sodium sulfate, the solvent was evaporated to obtain the residue, which was recrystallized from benzene-n-hexane, and there was obtained 450 mg (yield 41%) of 5-(3,4-methylenedioxybenzyl)-2-oxazolidone as colourless scaly crystals having a melting point of 98.5° - 100° C.

Elemental Analysis: as $C_{11}H_{11}NO_4$. Calculated (%): C: 59.72; H: 5.01; N: 6.33. Found (%): C: 59.44; H: 5.09; N: 6.24.

IR ($\nu_{max}^{CHCl_3}$ cm$^{-1}$) : 3380, 3470 (NH, OH), 1765 (OCON).

NMR (CDCl$_3$) δ : 2.79 (2H, t, Ar—CH$_2$); 3.10 - 3.61 (sH, m, N—CH$_2$) 4.60 (1H, t, —CH$_2$CHCH$_2$—) 5.76 (2H, S,

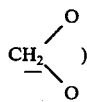

6.56 (3H, S, —C$_6$H$_3$).
MS (m/e) : 221 (M+).

EXAMPLE 12

5-(3,4-methylenedioxybenzyl)-3-phenyl-2-oxazolidone:

The mixture of 890 mg of safrole oxide, 1.65 g of ethyl N-phenylcarbamate and 100 mg of triethylamine was molten at 115° - 120° C for 2 hours. After the completion of the reaction, the mixture was dissolved in a small quantity of chloroform and washed with water. After drying over anhydrous sodium sulfate, the solvent was evaporated to obtain the residue, which was recrystallized from ethanol, there was obtained 1.05 g (yield 71%) of 5-(3,4-methylenedioxybenzyl)-3-phenyl-2-oxazolidone as colourless needles having a melting point of 110° - 111° C.

Elemental Analysis: as $C_{17}H_{15}NO_4$. Calculated (%): C: 68.67; H: 5.08; N: 4.71. Found (%): C: 68.47; H: 5.26; N: 4.79.

IR ($\nu_{max}^{CHCl_3}$ cm$^{-1}$) : 1610 (N—Ar), 1760 (OCON).
NMR (CDCl$_3$) δ : 3.00 (2H, m, Ar—CH$_2$). 3.60 - 4.04 (2H, m, N—CH$_2$) 4.79 (1H, t, —CH$_2$CHCH$_2$—) 5.92 (2H, S,

6.73 (3H, S, C$_6$H$_3$) 7.10 - 7.52 (5H, m, N—C$_6$H$_5$).
MS (m/e) : 297 (M+).

EXAMPLE 13

5-(o-chloro)benzyl-2-oxazolidone:

a. 16.6 g of o-chloroallylbenzene was dissolved in 100 ml of chloroform and to the mixture was added dropwise, while maintaining the temperature at 0° - 5° C, 25 g of m-chloroperbenzoic acid dissolved in 600 ml of chloroform. The resulting mixture was allowed to stand at the same temperature for 72 hours. After the separated m-chlorobenzoic acid was filtered off, the filtrate was washed with 10% sodium hydroxide solution, then with water and dried over anhydrous sodium sulfate. The solvent was evaporated to obtain the residue, which was distilled under reduced pressure to give 7.2 g (yield 38.8%) of o-chloroallylbenzene oxide having a boiling point of 93° C/3 mmHg.

IR ($\nu_{max}^{CHCl_3}$ cm$^{-1}$) : disappearance of vinyl group absorption, 3050 (methylene group of epoxy ring).

b. The mixture of 6.3 g of 0-chloroallylbenzene oxide, 33 g of ethylcarbamate and 3 ml of triethylamine was heated with stirring at 120° - 135° C for 4 hours. The resulting mixture was dissolved in benzene, washed with saturated sodium chloride solution and dried over anhydrous sodium sulfate. The solvent was evaporated to obtain the residue, which was chromatographed over a silica gel, and eluted with the mixed solvent of chloroform and methanol (200:1). The thus obtained product was recrystallized from diethyl ether, and there was obtained 3.7 g (yield 47.1%) of 5-(o-chloro)benzyl-2-oxazolidone having a melting point of 114° - 115° C.

IR ($\nu_{max}^{CHCl_3}$ cm$^{-1}$) : 3470 (NH), 1760 (OCON) NMR (CDCl$_3$) δ : 3.02 (2H, q, Ph—CH$_2$); 3.20 - 3.54 (2H, m, CH$_2$CHCH$_2$N); 4.72 (1H, m, CH$_2$CHCH$_2$); 6.42 (1H, S, NH); 6.98 (4H, m, aromatic protons).

EXAMPLE 14

5-(p-chloro)benzyl-2-oxazolidone:

a. 24.6 g of p-chloroallylbenzene was dissolved in 100 ml of chloroform and to the mixture was added dropwise, while maintaining the temperature at 0° - 5° C, 34.5 g of m-chloroperbenzoic acid dissolved in 1l of chloroform. The resulting mixture was allowed to stand at the same temperature for 72 hours. After the separated m-chlorobenzoic acid was filtered off, the filtrate was washed with 10% sodium hydroxide solution, then with water and dried over anhydrous sodium sulfate. The solvent was evaporated to obtain the residue, which was distilled under reduced pressure to give 15.1 g (yield 55.7%) of p-chloroallylbenzene oxide having a boiling point of 96° C/2.5 mmHg.

IR ($\nu_{max}^{CHCl_3}$ cm$^{-1}$) : disappearance of vinyl group absorption, 3050 (methylene group of expoxy ring).

b. The mixture of 14.2 g of p-chloroallylbenzene oxide, 90 g of ethyl carbamate and 5 ml of triethylamine was heated with stirring at 120° - 135° C for 3 hours. The resulting mixture was dissolved in benzene, washed with saturated sodium chloride solution and dried over anhydrous sodium sulfate. The solvent was evaporated to obtain the residue, which was recrystallized from ethyl acetate to give 13.4 g (yield 68.7%) of 5-(p- chloro)benzyl-2-oxazolidone as colourless needles having a melting point of 125° – 126° C.

Elemental Analysis: as $C_{10}H_{10}NO_2$ Cl. Calculated (%): C: 56.75, H: 4.76; N: 6.42. Found (%): C: 56.70; H: 4.68; N: 6.72.

IR ($\nu$ max$^{CHCl_3}$ cm$^{-1}$) : 3470 (>NH), 1760 (OCON).

NMR (CDCl$_3$) $\delta$ : 2.84 (2H, t, Ph—CH$_2$), 3.06 – 3.52 (2H, m, CH—CH$_2$—N<) ; 4.60 (1H, m, CH$_2$—CH—); 6.05 (1H, broad S, NH); 6.94(4H, q, aromatic protons);

MS (m/e) : 211 (M+). Example 15

5-(m-chlorobenzyl)-2-oxazolidone: (a) To 6.1 g of m-chloroallylbenzene was added 85 ml of chloroform solution containing perbenzoic acid and the mixture was allowed to stand at room temperature overnight. This solution was washed with sodium hydroxide solution, 20% Mohr's salt solution and then water, and dried over anhydrous sodium sulfate. The solvent was evaporated to obtain the residue, which was distilled under reduced pressure to give 2.2 g (yield 33%) of m-chloroallylbenzene oxide having a boiling point of 117° C/7 mmHg.

NMR (CDCl$_3$) $\delta$ : 2.20 – 3.00 (5H, m, —CH$_2$—X$_2$ and

6.70 – 7.16 (4H, m, aromatic protons)

b. The mixture of 2.2 g of m-chloroallylbenzene oxide, 13 g of ethyl carbamate and 1 ml of triethylamine was heated with stirring at 130° – 135° C for 3.5 hours. To the resulting mixture was added benzene and the thus obtained solution was washed with saturated sodium chloride solution several times, then water, and dried anhydrous sodium sulfate. The solvent was evaporated to obtain the residue, which was recrystallized from benzene, and benzene-n-hexane to give 720 mg (yield 26%) of 5-(m-chlorobenzyl)-2-oxazolidone having a melting point of 113° – 114° C.

IR ($\nu_{max}^{KBr}$ cm$^{-1}$) : 1740 – 1700 (CO)

NMR (CDCl$_3$) $\nu$ : 2.76 – 3.76 (4H, m, —CH$_2$—X$_2$) 4.68 – 5.00 (1H, m,

6.32 (1H, broad S, >NH), 7.40 – 7.80 (4H, m, aromatic protons).

MS (m/e) : 213, 211 (M+).

EXAMPLE 16

5-(p-fluorobenzyl)-2-oxazolidone:

a. 7 g of p-fluoroallylbenzene was added to 800 ml of chloroform solution containing perbenzoic acid prepared from 46 g of benzoyl peroxide and the mixture was allowed to stand at about 5° C for 5 days. The resulting mixture was washed with sodium hydroxide solution, water, Mohr's salt solution, then water, and dried over anhydrous sodium sulfate. The solvent was evaporated and the residue was distilled under reduced pressure to give 4.1 g (yield 52%) of p-fluoroallylbenzene oxide as colorless liquid.

NMR (CCl$_4$) $\delta$ : 2.28 – 3.08 (5H, m,

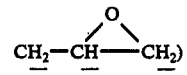

6.80 – 7.30 (4H, m, aromatic protons).

b. The mixture of 4.1 g of p-fluoroallylbenzene oxide, 2.67 g of ethyl carbamate and a few drops of triethylamine was heated with stirring at 150° C in an atmosphere of nitrogen for 5 hours. After cooling, to the reaction mixture was added chloroform and the resulting mixture was washed with water, dried over anhydrous sodium sulfate. The solvent was evaporated to obtain the residue, which was recrystallized from benzene-n-hexane to give 1.8 g (yield 33.1%) of 5-(p-fluorobenzyl)-2-oxazolidone having a melting point of 120.5 to 121° C as colorless needles.

IR ($\nu_{max}^{KBr}$ cm$^{-1}$) : 3250 (NH), 1720 and 1760 (broad).

NMR (CDCl$_3$) $\delta$ : 1.79 and 6.14 (1H, broad s, NH, disappeared by D$_2$O addition). 2.76 – 3.74 (4H, m, ArCH$_2$ and N—CH$_2$) 4.66 – 4.98 (1H, m, >CH—) 6.92 – 7.40 (4H, m, aromatic protons)

MS (m/e) : 195 (M+).

EXAMPLE 17

5-(o-bromobenzyl)-2-oxazolidone:

a. The mixture of 500 ml of chloroform, 5.2 g of o-bromoallylbenzene and perbenzoic acid prepared from 20 g of benzoylperoxide was allowed to stand at room temperature for 10 days. The resulting solution was washed with 10% sodium hydroxide solution, water Mohr's salt solution, then water, and dried over anhydrous sodium sulfate. The solvent was evaporated to obtain the residue, which was distilled under reduced pressure to give 2.2 g (yield 40%) of O-bromoallylbenzene oxide as colourless liquid.

NMR (CCl$_4$) $\delta$ : 2.32 – 3.16 (5H, m,

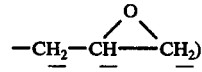

6.92 – 7.54 (4H, m, aromatic protons).

b. The mixture of 2.2 g. of o-bromoallylbenzene oxide, 900 mg of ethylcarbamate and three drops of triethylamine was heated with stirring in an atmosphere of nitrogen at 150° C for 5 hours. After the completion of the reaction, the reaction mixture was cooled and to this was added water. The resulting mixture was extracted with chloroform and the extract was dried over anhydrous sodium sulfate. The solvent was evaporated to obtain an oil substance, which was solidified by adding ether and hexane. This was recrystallized from benzene to give 650 mg (yield 25%) of 5-(o-bromobenzyl)-2-oxazolidone as colourless plates having a melting point of 130° – 131° C.

IR ($\nu_{max}^{KBr}$ cm$^{-1}$) : 3240 (NH), 1725 (C=O).

NMR (CDCl$_3$) $\delta$ : 1.88, 6.32 (1H, broad s, NH and OH), 2.98 – 3.76 (4H, m, CH$_2$—CH—CH$_2$), 4.80 – 5.08 (1H, m,

7.00 – 7.65 (4H, m, aromatic protons)

MS (m/e) : 255 (M+), 257 (M++2).

EXAMPLE 18

5-(p-bromobenzyl)-2-oxazolidone:

a. The mixture of 5.1 g of p-bromoallylbenzene, 8.5 g of m-chloroperbenzoic acid and 200 ml of chloroform was allowed to stand at about 5° C for 7 days. The resulting mixture was washed with 10% sodium hydroxide solution, water, Mohr's salt solution, then water, and dried over anhydrous sodium sulfate. The solvent was evaporated to obtain 4.8 g (yield 85%) of p-bromoallylbenzene oxide.

NMR (CCl$_4$) δ : 2.28 – 3.04 (5H, m,

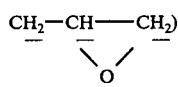

6.90 – 7.40 (4H, m, aromatic protons).

b. The mixture of 4.2 g of p-bromoallybenzene oxide, 2 g of ethylcarbamate and ten drops of triethylamine was heated with stirring in at atmosphere of nitrogen at 150° C for 5 hours. After the completion of the reaction, the resulting mixture was cooled and to this was added water. The mixture was extracted with chloroform and the extract was washed twice with water, then dried over anhydrous sodium sulfate. The solvent was evaporated to obtain the residue, which was solidified by adding ether. This was recrystallized from the mixed solvent of benzene and hexane to give 1.2 g (yield 24%) of 5-(p-bromobenzyl)-2-oxazolidone as pale yellow powdered crystals having a melting point of 115° – 117° C.

IR ($\nu_{max}^{KBr}$ cm$^{-1}$) : 3260 (NH), 1730, 1710 (NHCO).

NMR (CDCl$_3$) δ : 2.0, 6.28 (1H, broad s, N$\underline{H}$ and O$\underline{H}$), 2.90 – 3.70 (4H, m,

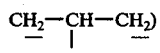

4.64 – 4.96 (1H, m,

7.40 – 7.50 (4H, m, aromatic protons)

EXAMPLE 19

5-(o-methylbenzyl)-2-oxazolidone:

a. To 300 ml of chloroform solution containing perbenzoic acid prepared from 36.3 g of benzoyl peroxide was added with ice-cooling, 6.6 g of O-allyltoluene dissolved in 20 ml of chloroform. The resulting mixture was allowed to stand at 5° C for 4 days and washed with 10% sodium hydroxide solution, water, Mohr's salt solution and then water, and dried over anhydrous sodium sulfate. The solvent was evaporated to obtain the residue, which was distilled under reduced pressure to give 2.8 g (yield 37.9%) of o-methylallylbenzene oxide as colourless liquid having a boiling point of 109° – 111° C/15 mmHg.

NMR (CDCl$_3$) δ : 2.12 – 3.08 (5H, m,

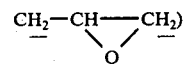

2.29 (3H, S, C$\underline{H_3}$), 7.08 (4H, S, aromatic protons).

b. The mixture of 740 mg of o-methylallylbenzene oxide, 445 mg of ethyl carbamate and 2.5 ml of triethylamine was heated with stirring at 130° C for 3.5 hours in a stream of nitrogen. After cooling, to the mixture was added water and the resulting mixture was extracted with chloroform. The extract was washed with water and dried over anhydrous sodium sulfate. The solvent was evaporated to obtain the residue, which was recrystallized from ethyl acetate to give 222 mg (yield 23.3%) of 5-(o-methylbenzyl)-2-oxazolidone having a melting point of 121° – 122° C.

IR ($\nu_{max}^{CHCl_3}$ cm$^{-1}$) : 3480 (NH), 1760 (CO).

NMR (CDCl$_3$) δ : 2.33 (3H, S, —C$\underline{H_3}$), 2.69 – 3.66 (4H, m, N—C$\underline{H_2}$ and Ar—C$\underline{H_2}$), 4.66 – 4.96 (1H, m, >C$\underline{H}$—), 6.24 (1H, broad S, —N$\underline{H}$), 7.11 (4H, S, aromatic protons).

EXAMPLE 20

5-(m-methylbenzyl)-2-oxazolidone:

a. To 5.3 g of m-methylallylbenzene was added 85 ml of chloroform solution containing perbenzoic acid and the mixture was allowed to stand at room temperature overnight. The resulting solution was washed with sodium hydroxide solution, Mohr's salt solution and then water, and dried over anhydrous sodium sulfate. The solvent was evaporated to obtain the residue, which was distilled under reduced pressure to give 1.1 g (yield 19%) of m-methylallylbenzene oxide having a boiling point of 90° C/7 mmHg.

b. The mixture of 3.1 g of m-methylallylbenzene oxide, 19 g of ethyl carbamate and 1.5 ml of triethylamine was heated with stirring at 135° – 140° C for 4 hours. After cooling, to the mixture was added benzene and the resulting solution was washed with water and dried over anhydrous sodium sulfate. The solvent was evaporated to obtain the residue, which was recrystallized from benzene-n-hexane to give 0.87 g (yield 22%) of 5-(m-methylbenzyl)-2-oxazolidone having a melting point of 89° – 90.5° C.

IR ($\nu_{max}^{KBr}$ cm$^{-1}$) : 1700 (CO).

NMR (CDCl$_3$) δ : b 2.30 (3H, S, —C$\underline{H_3}$) 2.60 – 3.64 (4H, m, —C$\underline{H_2}$—X2) 4.50 – 4.90 (1H, m,

6.36 (1H, broad S,

6.80 – 7.30 (4H, m, aromatic protons).

MS (m/e) : 191 (M+).

EXAMPLE 21

5-(p-methylbenzyl)-2-oxazolidone:

a. To chloroform solution containing perbenzoic acid prepared from 36.6 g of benzoyl peroxide was added, with ice-cooling, 6.6 g of p-allyltoluene dissolved in 20 ml of chloroform. The resulting mixture was allowed to stand at 5° C for 4 days and washed with 10% sodium hydroxide solution, water, Mohr's salt solution and then water, and dried over anhydrous sodium sulfate. The solvent was evaporated to obtain the residue, which was distilled under reduced pressure to give 35.3 g (yield 47.5%) of p-methylallylbenzene oxide as colourless liquid having a boiling point of 92° C/7 mmHg.

IR ($\nu_{max}^{CHCl_3}$ cm$^{-1}$) : disappearance of vinyl group absorption.

NMR (CDCl$_3$) δ : 2.28 (3H, S, —C$\underline{H}_3$) 2.20 - 3.04 (5H, m, benzyl protons and

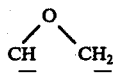

7.00 (4H, S. aromatic protons)

b. The mixture of 1.5 g of p-methylallylbenzene oxide, 4.5 g of ethyl carbamate and 0.5 ml of triethylamine was heated with stirring at 120° - 135° C for 3.5 hours. After cooling, the mixture was dissolved in 80 ml of benzene and the resulting solution washed with water and dried over anhydrous sodium sulfate. The solvent was evaporated to obtain the residue, which was recrystallized from benzene and then ethyl acetate to give 390 mg (yield 20.5%) of 5-(p-methylbenzyl)-2-oxazolidone as scaly cyrstals having a melting point of 144° - 146° C.

IR ($\nu_{max}^{CHCl_3}$ cm$^{-1}$) : 3480 (NH), 170 (CO).

NMR (CDCl$_3$) δ : 2.12 (3H, S, Ar, —C$\underline{H}_3$) 2.74 - 3.62 (4H, m, benzyl protons and

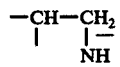

4.62 - 4.92 (1H, m,

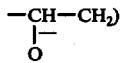

6.20 (1H, broad S, N$\underline{H}$) 7.10 (4H, S, aromatic protons).

EXAMPLE 22

5-(p-methylbenzyl)-2-oxazolidone:

The mixture of 1.5 g of p-methylallylbenzene oxide, 1.1 g of ethyl carbamate and 0.5 ml of triethylamine was heated with stirring at 150° C for 4 hours. After cooling, the mixture was dissolved in 150 ml of chloroform and the resulting solution washed with saturated sodium chloride solution and dried over anhydrous sodium sulfate. The solvent was evaporated to obtain the residue, which was recrystallized from ethyl acetate to give 830 mg (yield 43.5%) of 5-(p-methylbenzyl)-2-oxazolidone.

Values of R$_f$ and results in IR spectrum of this product are in accord with those of the compound obtained according to Example 21.

EXAMPLE 23

5-(o-ethylbenzyl)-2-oxazolidone:

a. 6.7 g of o-ethylallylbenzene was added to 100 ml chloroform solution containing perbenzoic acid prepared from 25 g of benzoyl peroxide and the mixture was allowed to stand at about 4° C for 4 days. The resulting mixture was washed with sodium hydroxide solution, Mohr's salt solution, then water and dried over anhydrous sodium sulfate. The solvent was evaporated and the concentration was distilled under reduced pressure to obtain 3.0 g (yield 40%) of o-ethylallyllbenzene oxide having a boiling point of 110° to 115° C/11 mmHg as oily substance.

b. To 3.0 g of o-ethylallylbenzene oxide was added 1.8 g of ethylcarbamate and a few drops of triethylamine and the mixture was heated at 145° to 150° C with stirring for about 5 hours. The resulting mixture was chromatographed on a silica gel, eluted with the mixed solvent of chloroform and methanol (100:1), and there was obtained a crude product. This was recrystallized from benzene-n-hexane to give 1.4 g of 5-(o-ethylbenzyl)-2-oxazolidone having a melting point of 104 to 105° C as colourless scaly crystals.

IR ($\nu_{max}^{KBR}$ cm$^{-1}$) : 3240 (NH), 1770, 1720 (CO).

NMR (CDCl$_3$) δ : 1.10 (3H, t, J=6Hz, —C$\underline{H}_3$) 2.64 (2H, q, J=6Hz, —C$\underline{H}_2$—CH$_3$) 2.76 - 3.68 (4H, m, —C$\underline{H}_2$ × 2) 4.60 - 4.96 (1H, m,

6.80 (1H, broad s, N$\underline{H}$) 6.72 - 7.24 (4H, m, aromatic protons).

MS (m/e) : 205 (M+).

EXAMPLE 24

5-(p-ethylbenzyl)-2-oxazolidone:

a. 3.8 g of p-ethylallylbenzene was added to 5.9 g of m-chloroperbenzoic acid dissolved in 70 ml of chloroform and the mixture was allowed to stand at about 5° C for 4 days. The resulting mixture was washed with sodium hydroxide solution, Mohr's salt solution, then water and dried over anhydrous sodium sulfate. The solvent was evaporated and the concentration was distilled under reduced pressure to obtain 1.8 g (yield 43%) of p-ethylallylbenzene oxide having a boiling point of 144° to 143° C/38 mmHg as oily substance.

b. To 1.8 g of p-ethylallylbenzene oxide was added 1.1 g of ethyl carbamate and a few drops of triethylamine and the mixture was heated with stirring at 145° to 150° C for about 5 hours. After cooling, the resulting mixture was recrystallized from ethyl acetate to give 550 mg of 5-(p-ethylbenzyl)-2-oxazolidone. The mother liquor was chromatographed on a silica gel, eluted with chloroform, and there was obtained a crude product. This was recrystallized from ethyl acetate to give 480 mg of 5-(p-ethylbenzyl)-2-oxazolidone having a melting point of 133° to 134° C as colourless scaly crystals.

IR ($\nu_{max}^{KBR}$ cm$^{-1}$) : 3240 (NH), 1760, 1720(C).

NMR (CDCl$_3$) δ : 1.22 (3H, t, J=6Hz, —C$\underline{H}_3$) 2.62 (2H, q, J=6Hz, —C$\underline{H}_2$—CH$_3$) 2.72 - 3.68 (4H, m, —C$\underline{H}_2$ × 2) 4.64 - 5.00 (1H, m,

6.90 - 7.32 (4H, m, aromatic protons).

EXAMPLE 25

5-(p-n-propylbenzyl)-2-oxazolidone:

a. To perbenzoic acid in chloroform prepared from 65.5 g of benzoylperoxide was added 1.45 g of p-allylpropylbenzene and the mixture was allowed to stand at 5° C for 6 days. After the completion of the reaction, the mixture was washed with 2% sodium hydroxide solution, water, Mohr's salt solution, then water, and dried over anhydrous sodium sulfate. The solvent was evaporated to obtain the residue, which was distilled under reduced pressure to give 12.1 g (yield 76%) of p-n-propylallylbenzene oxide as colourless liquid.

NMR (CCl₄) δ : 0.90 (3H, t, J=8Hz, CH₃CH₂CH₂—) 1.40 – 1.80 (2H, m, CH₃CH₂CH₂—) 2.28 – 3.04 (7H, m,

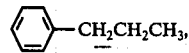

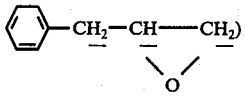

7.00 (4H, S, aromatic protons).

b. The mixture of 3.6 g of p-n-propylallylbenzene oxide, 2.2 g of ethylcarbamate and two drops of triethylamine was heated with stirring at 150° C for 5 hours. After the completion of the reaction, the mixture was cooled and dissolved in 60 ml of benzene. The resulting mixture was washed five times with water and dried over anhydrous sodium sulfate. The solvent was evaporated to obtain the residue, which was twice recrystallized from the mixed solvent of benzene and hexane to give 1.6 g (yield 37%) of 5-(p-n-propyl)-2-oxazolidone as colourless scaly crystals.

IR ($\nu_{max}^{KBr}$ cm⁻¹) : 3440 (NH), 1720, 1760 (CO).

NMR (CDCl₃) δ : 0.90 (3H, t, J=8Hz, CH₃CH₂CH₂—) 1.40 – 1.80 (2H, m, CH₃CH₂CH₂—) 2.50 (2H, t, J=8Hz,

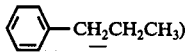

2.70 – 3.60 (4H, m,

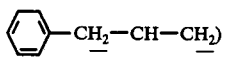

4.90 (1H, m,

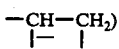

6.00 (1H, broad S, NH) 7.04 (4H, S, aromatic protons).
MS (m/e) : 219 (M+).

EXAMPLE 26

5-(p-isopropyl)-2-oxazolidone:

a. The mixture of 1.6 g of p-allylcumene, 4.2 fold moles of perbenzoic acid and chloroform was allowed to stand at 5° C for 10 days. After the completion of the reaction, the mixture was washed with 3% sodium hydroxide solution, water, Mohr's salt solution, then water, and dried over anhydrous sodium sulfate. The solvent was evaporated to obtain 1.8 g of p-isopropylallylbenzene oxide as colourless oily substance.

IR ($\nu_{max}^{CHCl_3}$ cm−1) : disappearance of absorption due to vinyl group.

NMR (CCl₄) δ : 1.30 (d, 6H, J=5Hz, CH(CH₃)₂) 2.30 – 3.00 (m, 5H, CH(CH₃)₂,

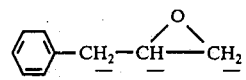

7.00 (s, 4H, aromatic protons).

b. The mixture of 1.4 g of p-isopropylallylbenzene oxide, 0.9 g of ethyl carbamate and two drops of triethylamine was heated with stirring in an atmosphere of nitrogen at 150° C for 5 hours. After cooling, to the mixture was added 50 ml of benzene and the resulting mixture was sufficiently washed with water, and dried over anhydrous sodium sulfate. The solvent was evaporated to obtain brownish oily substance, which was solidified by adding the mixed solvent of diethyl ether and petroleum ether and collected by filtration. This was twice recrystallized from the mixed solvent of benzene and hexane to give 110 mg of 5-(p-isopropyl)-2-oxazolidone as colourless scaly crystals having a melting point of 108° – 109° C.

IR ($\nu_{max}^{KBr}$ cm⁻¹) : 3460 (NH), 1760, 1720 (CO).

NMR (CDCl₃) δ : 1.24 (d, 6H, CH(CH₃)₂) 2.70 – 3.70 (m, 5H, CH(CH₃)₂,

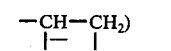

4.68 – 4.90 (m, 1H,

—CH—CH₂)
 |    |

5.48 (broad S, 1H, NH) 7.08 (s, 4H, aromatic protons).
MS (m/e) : 219 (M+).

EXAMPLE 27

5-(o-methoxy)benzyl-2-oxazolidone:

a. 25 g of o-hydroxyallylbenzene was dissolved in 100 ml of water and to the mixture was added 8g of sodium hydroxide. To the resulting mixture was added dropwise 25.2 g of dimethyl sulfate over a period of about 2 hours, while maintaining the temperature at 5° – 10° C. The thus obtained mixture was heated with stirring at 80°– 100° C for approximately 30 minutes, and then the oil layer was separated. This layer was distilled under reduced pressure, there was obtained 22.3 g (yield 81%) of o-methoxyallylbenzene having a boiling point of 51° C/2 mmHg.

IR ($\nu_{max}^{CHCl_3}$ cm⁻¹) : 2845 (OCH₃), disappearance of OH absorption.

b. 22.2 g of o-methoxyallylbenzene was dissolved in 200 ml of chloroform and to the mixture was added dropwise, while maintaining the temperature at 0° – 5° C, 31.3 g of m-chloroperbenzoic acid dissolved in 1l of chloroform. The thus obtained mixture was allowed to stand for 55 hours at the same temperature. After separated m-chlorobenzoic acid was filtered off, the filtrate was washed with 5% sodium hydroxide solution, then with water and dried over anhydrous sodium sulfate. The solvent was evaporated under reduced pressure to obtained the residue, which was distilled under reduced pressure, there was obtained 26.8 g (yield 54.5%) of o-methoxyallylbenzene oxide having a boiling point of 88.5° – 89.5° C/1 mmHg.

IR ($\nu_{max}^{CHCl_3}$ cm$^{-1}$) : disappearance of vinyl group absorption.

c. The mixture of 820 mg of o-methoxyallylbenzene oxide, 2.3 g of ethyl carbamate and 100 mg of triethylamine was heated with stirring at 120° – 130° C for 3 hours. After the completion of the reaction, the mixture was dissolved in benzene, washed with water and dried over anhydrous sodium sulfate. The solvent was evaporated to obtain the residue, which was chromatographed over a silica gel, and eluted with the mixed solvent of chloroform and methanol (100:1). The thus obtained product was recrystallized from diethyl ether-petroleum ether, and there was obtained 400 mg (yield 40%) of 5-(o-methoxy)benzyl-2-oxazolidone as colourless prismatic crystals having a melting point of 64° – 66° C.

Elemental Analysis:as $C_{11}H_{13}NO_3$. Calculated (%): C: 63.75, H: 6.32, N: 6.76. Found (%):C: 63.73, H: 6.40, N: 6.59.

IR ($\nu_{max}^{CHCl_3}$ cm$^{-1}$) : 3470, 3270 (NH, OH), 1760 (OCON).

NMR (CDCl$_3$) : 2.98 (2H, m, Ar—CH$_2$) 3.10 – 3.50 (2H, m, CH$_2$—CH—CH$_2$—N) 3.54 (3H, S, OCH$_3$) 4.80 (1H, m, CH$_2$CHCH$_2$) 6.44 (1H, broad S, NH) 6.68 – 7.18 (4H, m, C$_6$H$_4$).

MS (m/e) : 207 (M+).

EXAMPLE 28

5-(p-methoxy)benzyl-2-oxazolidone:

a. 22.2 g of p-methoxyallylbenzene was dissolved in 200 ml of chloroform and to the mixture was added dropwise, while maintaining the temperature at 0° –5° C, 31.3 g of m-chloroperbenzoic acid dissolved in 1l of chloroform. The resulting mixture was allowed to stand at the same temperature for 40 hours. After the separated m-chlorobenzoic acid was filtered off, the filtrate was washed with 5% sodium hydroxide solution, then with water and dried over anhydrous sodium sulfate. The solvent was evaporated under reduced pressure to obtain the residue, which was distilled under reduced pressure, there was obtained 15.4 g (yield 62.6%) of p-methoxyallylbenzene oxide having a boiling point of 90° C/2 mmHg.

IR ($\nu_{max}^{CHCl_3}$ cm$^{-1}$) : disappearance of vinyl group absorption.

b. The mixture of 14.5 g of p-methoxyallylbenzene oxide, 80 g of ethyl carbamate and 4 g of triethylamine was heated with stirring at 120° – 130° C for 4 hours. The resulting mixture was dissolved in benzene. After cooling, the mixture was washed with water and dried over anhydrous sodium sulfate. The solvent was evaporated under reduced pressure to obtain the white powder, which was recrystallized from benzene to give 9.3 g (yield 50.8%) of 5-(p-methoxy)benzyl-2-oxazolidone as colourless needles having a melting point of 120.5 – 123° C.

Elemental Analysis:as $C_{11}H_{13}NO_3$. Calculated (%): C:63.75, H: 6.32, N: 6.76. Found (%):C: 63.70, H: 6.33, N: 6.79.

IR ($\nu_{max}^{CHCl_3}$ cm$^{-1}$): 3470, 3380 (NH, OH), 1760 (CO).

MS(m/e) : 207 (M+).

NMR (CDCl$_3$) δ : 2.86 (2H, m, Ar—CH$_2$) 3.20 – 3.68 (2H, m, CH—CH$_2$—N) 3.69 (3H, S, —OCH$_3$) 4.67 (1H, m, CH$_2$—CH—CH$_2$—) 6.12 (1H, broad S, NH) 6.56 – 7.20 (4H, m, C$_6$H$_4$).

EXAMPLE 29

5-(o-ethoxy)benzyl-2-oxazolidone:

a. To the chloroform solution containing perbenzoic acid prepared from 29 g of benzoyl peroxide was added 6.5 g of o-methoxyallylbenzene dissolved in 20 ml of chloroform, and the mixture was allowed to stand at 0° – 5° C for 3 days. The resulting mixture was washed with 10% sodium hydroxide solution, Mohr's salt solution and then water, and dried over anhydrous sodium sulfate. The solvent was evaporated to obtain the residue, which was distilled under reduced pressure to give 2.9 g (yield 41%) of 2-ethoxyallylbenzene oxide as pale yellow clear liquid having a boiling point of 120° – 121° C/9 mmHg.

IR ($\nu_{max}^{CHCl_3}$ cm$^{-1}$) : disappearance of vinyl group absorption.

NMR (CDCl$_3$) δ : 1.40 (3H, t, d=4Hz, —CH$_2$CH$_3$) 2.30 – 3.10 (5H, m, benzyl protons and

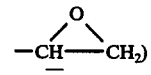

4.00 (2H, q, d=4Hz, —CH$_2$CH$_3$) 6.60 – 7.20 (4H, m, aromatic protons).

b. The mixture of 0.9 g of o-ethoxyallylbenzene oxide, 0.5 ml of triethylamine and 4.5 g of ethyl carbamate was heated with stirring at 120° – 135° C for 4 hours. After cooling, the resulting mixture was dissolved in 50 ml of benzene and this solution was washed with water and dried over anhydrous sodium sulfate. The solvent was evaporated to obtain the residue, which was chromatographed over a silica gel, and eluted with the mixed solvent of chloroform and methanol (50:1) to give 0.5 g (yield 45%) of 5-(o-ethoxy)benzyl-2-oxazolidone as pale yellow liquid.

IR ($\nu_{max}^{CHCl_3}$ cm$^{-1}$) : 3470 (NH), 1745 (CO).

NMR (CDCl$_3$) δ : 1.32 (3H, t, d=3Hz, CH$_2$CH$_3$), 2.60 – 3.44 (4H, m, benzyl protons and —CH—CH$_2$—N), 3.90 (2H, q, d=3Hz, —CH$_2$CH$_3$) 4.50 – 4.80 (1H, m,

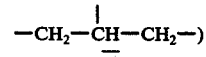

6.56 – 7.16 (5H, m, NH and aromatic protons).

EXAMPLE 30

5-(m-trifuoromethylbenzyl)-2-oxazolidone:

a. 7.4 g of m-trifluoromethylallylbenzene was added to chloroform solution containing perbenzoic acid prepared from 29.3 g of benzoyl peroxide and the mixture was allowed to stand at about 5° C for 7 days. After the completion of reaction, the resulting mixture was washed with sodium hydroxide solution, water, Mohr's salt solution, then water, and dried over anhydrous sodium sulfate. The solvent was evaporated and the concentrated was distilled under reduced pressure, there was obtained 6.2 g (yield 77%) of m-trifluoromethylallylbenzene oxide having a boiling point of 110° – 111° C/23 mmHg as colourless liquid.

IR ($\nu_{max}^{CHCl_3}$ cm$^{-1}$) : disappearance of vinyl group absorption.

NMR (CCl$_4$) δ : 2.28 – 3.04 (5H, m,

Ar—CH$_2$—CH——CH$_2$)
\\_/
O 7.30 -7.52 (4H, m, aromatic protons).

b. To 2.0 g of m-trifluoromethylallylbenzene oxide was added 1.1 g of ethyl carbamate and a few drops of triethylamine and the mixture was heated with stirring at 150° C for 4 hours. After cooling, the resulting mixture was dissolved in benzene and the solution was fully washed with water, dried over anhydrous sodium sulfate. The solvent was evaporated and the concentration was chromatographed on a silica gel, and there was obtained a white powder. This was recrystallized from benzene-n-hexane to give 633 mg (yield 26%) of 5-(m-trifuoromethylbenzyl)-2-oxazolidone having a melting point of 112° to 112.5° C.

IR ($\nu_{max}^{CHCl_3}$ cm$^{-1}$) : 3480 (NH), 1760 (CO).

NMR (CDCl$_3$) δ : 3.00 – 3.72 (4H, m,

—CH$_2$—CH—CH$_2$)

4.70 – 5.00 (1H, m,

CH—CH$_2$)

5.50 – 5.70 (1H, broad s, NH) 7.34 – 7.62 (4H, m, aromatic protons).

MS (m/e) : 245 (M+).

EXAMPLE 31

5-(o-trifluoromethylbenzyl)-2-oxazolidone:

a. The mixture of 6.0 g of o-trifluoromethylbenzene and 50 ml of chloroform was added to 8.4 g of m-chloroperbenzoic acid dissolved in 250 ml of chloroform and the resulting mixture was allowed to stand at about 5° C for 5 days. The formed m-chlorobenzoic acid was filtered off and the thus obtained solution was washed with sodium hydroxide solution, water, Mohr's salt solution, then water, dried over anhydrous sodium sulfate. The solvent was evaporated and the concentration was distilled under reduced pressure to obtain 4.5 g (yield 69%) of o-trifluoromethylallylbenzene oxide having a boiling point of 79° to 80° C/8 mmHg as colourless liquid.

IR ($\nu_{max}^{CHCl_3}$ cm$^{-1}$) : disappearance of vinyl group absorption.

NMR (CCl$_4$) δ : 2.32 – 3.30 (5H, m,

CH$_2$—CH——CH$_2$)
\\_/
O 7.20 – 7.70 (4H, m, aromatic protons).

b. To 2.0 g of o-trifluoromethylallylbenzene oxide was added 1.1 g of ethyl carbamate and a few drops of triethylamine and the mixture was heated with stirring at 150° C for 4.5 hours. After cooling, the mixture was dissolved in benzene and the resulting solution was fully washed with water, dried over anhydrous sodium sulfate. The solvent was evaporated to obtain the residue which was chromatographed on a silica gel, and there was obtained a white powder. This was recrystallized from benzene to give 685 mg (yield:28%) of 5-(o-trifluoromethylbenzyl)-2-oxazolidone having a melting point of 141.5° to 143° C as colourless granules.

IR ($\nu_{max}^{CHCl_3}$ cm$^{-1}$) : 3480 (NH), 1760 (CO).

NMR (CDCl$_3$) δ : 3.14 – 3.80 (4H, m,

—CH$_2$—CH—CH$_2$)

4.70 – 5.04 (1H, m, —CH—CH$_2$) 5.80 – 6.00 (1H, m, broad s, NH) 7.37 – 7.80 (4H, m, aromatic protons).

MS (m/e) : 245 (M+).

EXAMPLE 32

5-(o-phenoxybenzyl)-2-oxazolidone:

a. 5.8 g of o-phenoxyallylbenzene was added to 70 ml of chloroform solution containing perbenzoic acid prepared from 17 g of benzoyl peroxide and the mixture was allowed to stand at about 5° C for 4 days. The resulting mixture was washed with sodium hydroxide solution, Mohr's salt solution, then water and dried on anhydrous sodium sulfate. The solvent was evaporated and the concentrated was chromatographed over a silica gel, eluted with benzene, there was obtained 3.6 g (yield 58%) of o-phenoxyallylbenzene oxide.

IR ($\nu_{max}^{CHCl_3}$ cm$^{-1}$) : 1580 (aromatic vinyl), 1260 -1240 (—O—).

NMR (CCl$_4$) δ : 2.28 – 3.12 (5H, m, —CH$_2$ × 2 and

—CH—)

6.68 – 7.24 (9H, m, aromatic protons).

b. To 3.6 g of o-phenoxyallylbenzene oxide was added 1.5 g of ethyl carbamate and a few drops of triethylamine and the mixture was heated with stirring at 150° to 155° C for about 5 hours. After cooling to this was added benzene and the resulting mixture was washed with water, dried over anhydrous sodium sulfate. The solvent was evaporated and the concentration was chromatographed over a silica gel, eluted with the mixed solvent of chloroform and methanol (100:1), and there was obtained an oily substance. This was crystallized from diethyl ether to give 1.6 g (yield 37%) of 5-(o-phenoxybenzyl)-2-oxazolidone having a melting point of 100° to 101° C as colourless powdered crystals.

IR ($\nu_{max}^{KBr}$ cm$^{-1}$) : 3280 (NH), 1760 – 1740 (CO).

NMR (CCl$_4$) δ : 2.70 – 3.60 (4H, m, —CH$_2$ ×2) 4.76 – 4.96 (1H, m,

—CH—)

6.64 – 7.50 (10H, m, aromatic protons and NH, disappeared NH protons by D$_2$O addition).

MS (m/e) : 269 (M+).

EXAMPLE 33

5-(p-phenoxybenzyl)-2-oxazolidone:

a. To 6.3 g of p-phenoxyallylbenzene was added 45 ml of chloroform solution containing perbenzoic acid prepared from 11 g of benzoylperoxide, and the resulting mixture was allowed to stand at about 5° C for 5 days. The thus obtained solution was washed with 10% sodium hydroxide solution, Mohr's salt solution, then water, and dried over anhydrous sodium sulfate. The solvent was evaporated to obtain the residue. This was chromatographed over a silica gel, and eluted with chloroform, and there was obtained 2.7 g (yield 40%) of p-phenoxyallylbenzene oxide as an oily substance.

NMR (CCl₄) δ : 2.16 – 3.00 (5H, m, $$-CH_2-\overset{O}{\overset{\diagup\diagdown}{CH-CH_2}})$$

6.40 – 7.30 (9H, m, aromatic protons).

b. The mixture of 2.6 g of p-phenoxyallylbenzene oxide, 1.4 g of ethyl carbamate and several drops of triethylamine was heated with stirring at 150° – 160° C for 5 hours. After cooling, to the mixture was added benzene and the resulting mixture was washed with water, and dried over anhydrous sodium sulfate. The solvent was evaporated to obtain the residue, which was recrystallized from the mixed solvent of benzene and n-hexane to give 1.0 g of 5-(p-phenoxybenzyl)-2-oxazolidone was colourless needles having a melting point of 118° – 119° C.

IR ($\nu_{max}^{KBr}$ cm⁻¹) : 3300 (NH), 1760, 1740 (CO).

NMR (CDCl₃) δ : 2.70 – 3.76 (4H, m, —C$\underline{H}_2$—X2) 4.63 – 5.04 (1H, m, $$-\overset{|}{\underline{CH}}-)$$

6.24 (broad s, 1H, NH, disappeared by D₂O, 6.88 – 7.96 (9H, m, aromatic protons).

EXAMPLE 34

5-(o-benzylbenzyl)-2-oxazolidone:

a. To perbenzoic acid in chloroform prepared from 15 g of benzoylperoxide was added 6.0 g of o-benzylallylbenzene and the mixture was allowed to stand at 5° C for 3 days. The mixture was washed with 2% sodium hydroxide solution, Mohr's salt solution, then water, and dried over anhydrous sodium sulfate. The solvent was evaporated to obtain the residue, which was chromatographed over a silica gel, and as eluted with benzene/n-hexane (1/1), there was obtained 1.5 g of o-benzylallylbenzene oxide as an oily substance.

b. The mixture of 1.6 g of o-benzylallylbenzene oxide, 0.6 g of ethyl carbamate and several drops of triethylamine was heated with stirring at 145° – 155° C for 5 hours. The mixture was chromatographed over a silica gel, and eluted with chloroform/methanol (20/1), and there were obtained crystals. These cyrstals were recrystallized from the mixed solvent of benzene and n-hexane to give 1.0 g of 5-(o-benzylbenzyl)-2-oxazolidone as colourless needles having a melting point of 105° – 106.5° C.

IR ($\nu_{max}^{KBr}$ cm⁻¹) : 3240 (NH), 1750, 1700 (CO).

NMR (CDCl₃) δ : 2.60 – 3.44 (4H, m, —C$\underline{H}_2$-X2); 3.92 (2H, S, $$-\underline{CH}_2-\!\!\langle\bigcirc\rangle)$$

4.30 – 4.64 (1H, m, $$-\overset{|}{\underline{CH}}-)$$

6.20 (1H, broad S, N$\underline{H}$); 6.80 – 7.24 (9H, m, aromatic protons).

MS (m/e) : 267 (M+).

EXAMPLE 35

5-(o-phenylbenzyl)-2-oxazolidone:

a. 7.8 g of o-phenylallylbenzene was added to 120 ml of chloroform solution containing perbenzoic acid prepared from 25 g of benzoyl peroxide and the mixture was allowed to stand at about 5° C for 4 days. The resulting mixture was washed with sodium hydroxide solution, Mohr's salt solution, then water, and dried over anhydrous sodium sulfate. The solvent was evaporated and the residue was distilled under reduced pressure to obtain a fraction having a boiling point of 145° to 155° C/3 mmHg, which was chromatographed on a silica gel, eluted with chloroform, and there was obtained 6.0 g (yield 71%) of o-penylallylbenzene oxide as an oily substance.

NMR (CCl₄) δ : 2.02 – 2.20 (1H, m); 2.38 – 2.56 (1H, m); 2.60 – 2.90 (3H, m); 7.06 – 7.46 (9H, m, aromatic protons).

b. To 4.2 g of o-phenylallybenzene oxide was added 2.1 g of ethyl carbamate and a few drops of triethylamine and the mixture was heated with stirring at 145° to 150° C for 4 hours. After cooling, the mixture was washed with water and dried over anhydrous sodium sulfate. The solvent was evaporated and the residue was chromatographed on a silica gel, eluted with the mixed solvent of chloroform and methanol (100:1). The thus obtained product was recrystallized from ethanol to give 990 mg (yield 20%) of 5-(o-phenylbenzyl)-2-oxazolidone having a melting point of 146° to 147.5° C.

IR ($\nu_{max}^{KBr}$ cm⁻¹) : 3220 (NH), 1760 – 1740 (CO)

NMR (CDCl₃) δ : 2.76 – 3.50 (4H, m, -C$\underline{H}_2$x 2) 4.40 – 4.76 (1H, m, $$-\overset{|}{\underline{CH}}-)$$

5.60 – 5.90 (1H, broad s, N$\underline{H}$) 6.10 – 7.60 (9H, m, aromatic protons)

MS (m/e) : 253 (M+).

EXAMPLE 36

5-(o-benzyloxybenzyl)-2-oxazolidone:

a. 5.4 g of o-benzyl-1-allylphenol was added to 600 ml of chloroform solution containing perbenzoic acid prepared from 26.4 g of benzoyl peroxide and the mixture was allowed to stand at about 5° C for 4 days. The reslting mixture was washed with sodium hydroxide solution, water, Mohr's salt solution, then saturated sodium chloride solution, and dried over anhydrous sodium sulfate. The solvent was evaporated to obtain the residue which was distilled under reduced pressure, and there was obtained 4.1 g (yield 70.1%) of o-benzyloxyallylbenzene oxide having a boiling point of 158° to 160° C/5 mmHg as colourless oil.

NMR (CCl₄) δ : 2.26 – 3.12 (5H, m,

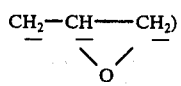

4.98 (2H, s, ArOC$\underline{H_2}$); 6.68 - 7.44 (9H, m, aromatic protons).

b. To 18 g of o-benzyloxyallylbenzene oxide was added 6.75 g of ethyl carbamate and a few drops of triethylamine and the mixture was heated with stirring at 150° C for 8 hours in an atmosphere of nitrogen. After cooling, to the reaction mixture was added water. The resulting mixture was extracted with chloroform and the extract was dried over anhydrous sodium sulfate. The solvent was evaporated and the concentrated was chromatographed on a silica gel, eluted with the mixed solvent of chloroform and benzene (2:1), and there was obtained a crude product. This was recrystallized from benzene-n-benzene to give 9.9 g (yield 39%) of 5-(o-benzyloxybenzyl)-2-oxazolidone having a melting point of 90° to 91° C as colourless prismatic crystals.

IR ($\nu_{max}^{CHCl_3}$ cm$^{-1}$) : 1755 (CO), 3480 (NH).

NMR (CDCl$_3$) δ : 2.82 - 3.66 (4H, m, M-CH$_2$ and ArCH$_2$C) 4.72 - 5.00 (1H, m, >CH-) 5.05 (2H, s, ArCH$_2$O) 6.20 (1H, broad s, NH) 6.78 - 7.47 (9H, m, aromatic protons).

EXAMPLE 37

5-(o-hydroxybenzyl)-2-oxazolidone:

The mixture of 7 g of 5-(o-benzyloxybenzyl)-2-oxazolidone as prepared in Example 36, 5 drops of 36% hydrochloric acid solution, 1.5 g of 5% palladium-carbon and 70 ml of ethanol was stirred at room temperature for 6 hours in an atmosphere of hydrogen. The palladium-carbon was filtered off using celite and the solvent was evaporated to obtain an oily substance, which was transformed to white solid by treatment with n-hexane. This was recrystallized from chloroform-benzene to give 2 g (yield 88%) of 5-(o-hydroxybenzyl)-2-oxazolidone having a melting point of 93° to 95° C as colourless prismatic crystals.

IR ($\nu_{max}^{KBr}$ cm$^{-1}$) : 3280, 3320 (NH and OH), 1720 (CO).

NMR (CDCl$_3$ + CF$_3$COOH)δ : 2.92 - 3.90 (4H, m, ArCH$_2$ and N-CG$_2$). 4.98 - 5.32 (1H, m, >CH—O) 6.56 - 7.24 (6H, m, aromatic protons, NH and OH).

MS (m/e) : 193 (M+).

EXAMPLE 38

5-(o-acetoxybenzyl)-2-oxazolidone:

To the mixture of 1.16 g of 5-(o-hydroxybenzyl)-2-oxazolidone as prepared in Example 37, 4.14 g of potassium carbonate and 20 ml of acetone was added dropwise 2.95 g acetyl bromide with stirring at 0° C. After dropping, the mixture was further stirred at room temperature for 4 hours. After the completion of reaction, the inorganic substance was filtered off and the solvent was evaporated. To the residue was added water and the resulting mixture was extracted with chloroform. The extract was dried over anhydrous sodium sulfate and the solvent was evaporated to obtain the residue. This was recrystallized from benzene-n-hexane to give 1.1 g (yield 70.8%) of 5-(o-acetoxybenzyl)-2-oxazolidone having a melting point of 98° to 99° C as colourless needles.

IR ($\nu_{max}^{KBr}$ cm$^{-1}$) : 3250 (NH), 1755 (OCOCH$_3$), 1740 (CONH).

NMR (CDCl$_3$)δ : 1.74 and 5.96 (1H, broad s, NH and OH), disappeared by D$_2$O addition), 2.32 (3H, s, CH$_3$), 2.70 - 3.60 (4H, m, ArCH$_2$ and N—CH$_2$), 4.66 - 4.92 (1H, m, >CH-O) 6.98 - 7.42 (4H, m, aromatic protons).

MS (m/e) : 235 (M+).

EXAMPLE 39

5-(o-allyloxybenzyl)-2-oxazolidone:

The mixture of 965 mg of 5-(o-hydroxybenzyl)-2-oxazolidone as prepared in Example 37, 759 mg of potassium carbonate, 605 mg of allyl bromide and 10 ml of acetone was heated with stirring under reflux condition in an atmosphere of nitrogen for 12 hours. After cooling, the inorganic substance was filtered off and the solvent was evaporated to obtain the residue. This was chromatographed on a silica gel, eluted with the mixed solvent of benzene and chloroform (1:2), and there was obtained 5-(o-allyloxybenzyl)-2-oxazolidone as colourless oil.

IR ($\nu_{max}^{CHCl_3}$ cm$^{-1}$) : 3480 (NH), 1755 (CO).

NMR (CDCl$_3$)δ : 1.98 and 6.20 (1H, broad s, NH, disappeared by D$_2$O addition). 2.82 - 3.67 (4H, m, ArCH$_2$ and N—CH$_2$), 4.44 - 4.58 (2H, m, OCH$_2$), 4.74 - 5.04 (1H, m, >CH-), 5.16 - 5.28 (2H, m, =CH$_2$), 5.82 - 6.10 (1H, m, -CH=), 6.73 - 7.30 (4H, m, aromatic protons).

MS (m/e) : 233 (M+).

EXAMPLE 40

5-(o-benzoylbenzyl)-2-oxazolidone:

a. To 12.0 g of o-allylbenzophenone ethylene ketal was added perkenzoic acid in chloroform prepared from 18 g of benzoyl peroxide and the resulting mixture was allowed to stand at about 5° C for 5 days. This solution was washed with 10% sodium hydroxide solution, Mohr's salt solution, then water, and dried over anhydrous sodium sulfate. The solvent was evaporated to obtain 12.0 g of o-(α,α-ethylenedioxybenzl)-allylbenzene oxide as an oily substance.

NMR (CCl$_4$) δ : 2.08 - 2.80 (5H, m,

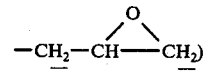

3.96 - 4.08 (4H, m, —O—C$\underline{H_2}$—C$\underline{H_2}$—O—), 6.90 -7.80 (9H, m, aromatic protons).

b. The mixture of 12.0 g of o-(α,α-ethylenedioxybenzyl)-allylbenzene oxide, 2.9 g of ethyl carbamate and several drops of triethylamine was heated with stirring at 150° - 155° C for 7.5 hours. The mixture was several times chromatographed over a silica gel, and eluted with chloroform/methanol (100/1), and there was obtained 1.6 g. of 5-[o-(α,α-ethylenedioxybenzyl) benzyl]-2-oxazolidone as an oily substance.

IR ($\nu_{max}^{CHCl_3}$ cm$^{-1}$) : 3470 (NH), 1750 (CO).

c. To 1.1 g of 5-[o-(α,α-ethylenedioxybenzl) benzyl]-2-oxazolidone were added 12 ml of acetone and 0.2 g of p-toluenesulfonic acid and the resulting solution was stirred overnight. Then to this was added benzene and the mixture was washed with diluted sodium hydroxide solution, then water, and dried over anhydrous sodium sulfate. The solvent was evaporated to obtain 1.06 g of 5-(o-benzoylbenzyl)-2-oxazolidone.

IR ($\nu_{max}^{CHCl_3}$ cm$^{-1}$) : 3470 (NH), 1750, 1660 (CO).

MS (m/e) : 181 (M+).

EXAMPLE 41

5-(o-acetylbenzyl)-2-oxazolidone:

a. The mixture of 1 g of o-allylacetophenone ethylene ketal, perbenzoic acid prepared from 3.6 g of benzoylperoxide and 100 ml of chloroform was allowed to stand at 5° C for 8 days. The resulting mixture was washed with 10% sodium hydroxide solution, water, Mohr's salt solution, then water, and dried over anhydrous sodium sulfate. The solvent was evaporated to obtain o-(α,α-ethylenedioxyethyl) benzylallylbenzene oxide as pale brownish oily substance.

NMR (CCl$_4$) δ : 1.62 (3H, s, CH$_3$), 2.20 - 3.20 (5H, m,

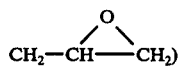

7.00 - 7.60 (4H, m, aromatic protons).

b. The mixture of 7.2 g of o-(α,α-ethylenedioxyethyl)benzylallylbenzene oxide, 3.2 g of ethyl carbamate and the drops of triethylamine was heated with stirring in an atmosphere of nitrogen at 150° C for 5 hours. After cooling, the reaction mixture was added to water and extracted with chloroform. The extract was dried over anhydrous sodium sulfate and freed of the solvent to obtain the oily substance which was solidified. This was washed with ether and n-hexane and recrystallized from the mixed solvent of benzene and n-hexane to give 1 g (yield 94%) of 5-[O-(α,α-ethylenedioxyethyl)benzyl]-b 2-oxazolidone as colourless needles having a melting point of 109° - 110° C.

IR ($\nu_{max}^{KBr}$ cm$^{-1}$) : 3240 (NH), 1730 (CO).

NMR (CDCl$_3$) δ : 1.63 (3H, s, CH$_3$), 2.08 and 6.45 (1H, broad s, NH and OH), 3.08 - 4.10 (9H, m, -OCH$_2$CH$_2$-O- and CH$_2$CHCH$_2$, 7.00 - 7.60 (4H, m, aromatic protons).

Elemental Analysis: as C$_{14}$H$_{14}$O$_4$N. Calculated (%) : C: 63.86 H: 6.51 N: 5.32. Found (%) : C: 64.10, H: 6.77, N: 5.61.

c. The mixture of 1.5 g of 5-[o-(α,α-ethylenediozyethyl)benzyl]-2-oxazolidone, 2.0 ml of anhydrous acetone and 100 mg of p-toluene-sulfonic acid was refluxed with stirring in an atmosphere for 3 hours. The solvent was evaporated to obtain the residue, to which was added saturated sodium bicarbonate solution. The resulting mixture was extracted with chloroform and the extract was dried over anhydrous sodium sulfate. The solvent was evapoarated to obtain 1.3 g of oily substance, which was recrystallized from the mixed solvent of benzene and n-hexane to give 1 g of 5-(o-acetylbenzyl)-2-oxazolidone as colourless prismatic crystals having a melting point of 85° - 86° C.

IR ($\nu_{max}^{KBr}$ cm$^{-1}$) : 3240 (NH), 1730 (CO), 1680 (CO).

NMR (CDCl$_3$) δ : 1.94 and 6.10 (1H, broad s, NH and OH), 2.58 (3H, s, CH$_3$), 3.00 - 3.80 (5H, m, CH$_2$-CH-CH$_2$) 4.70 - 5.00 (1H, m,

7.18 - 7.80 (4H, m, aromatic protons).

EXAMPLE 42

5-(o-fluorobenzyl)-2-oxazolidone:

The mixture of 1 g of o-fluoropropylbenzene-β,γ-diol and 700 mg of urea was rapidly heated to 190° C and at the same temperature was stirred in an atmosphere of nitrogen for 5 hours. After cooling, to the mixture was added water, and the resulting solution was extracted with chloroform and the extract was dried over anhydrous sodium sulfate. The solvent was evaporated to obtain the residue, which was chromatographed over a silica gel, and as eluted with chloroform, there was obtained crystals. These crystals were recrystallized from the mixed solvent of benzene and n-hexane to give 150 mg of 5-(o-fluorobenzyl)-2-oxazolidone as colourless plates having a melting point of 113° - 113.5° C.

IR ($\nu_{max}^{KBr}$ cm$^{-1}$) : 3250 (NH), 1720, 1710 (CO).

NMR (CDCl$_3$) : 1.84 and 6.30 (1H, broad s, NH, OH), 3.04 - 3.80 (4H, m, CH$_2$-CH-CH$_2$), 4.80 - 5.10 (1H, m, O-CH=), 7.00 - 7.50 (4H, m, aromatic protons).

MS (m/e) : 195 (M+).

EXAMPLE 43

5-(m-bromobenzyl)-2-oxazolidone:

The same procedure was repeated as in the example 15, and there was obtained 5-(m-bromobenzyl)-1-oxazolidone having a melting point of 122°-123.5° C.

IR($\nu_{max}^{KBr}$ cm$^{-1}$): 3300 (NH), 1750, 1710 (CO),

NMR(CDCl$_3$)δ : 2.64 - 3.80 (4H, m, -CH$_2$× 2) 4.68 - 5.04 (1H, m,

6.10 (1H, broad s, NH) 7.00 - 7.72 (4H, m, aromatic protons).

MS(m/e) : 257, 255 (M+).

EXAMPLE 44

5-(m-fluorobenzyl)-2-oxazolidone:

The same procedure was repeated as in the example 15, and there was obtained 5-(m-fluorobenzyl)-2-oxazolidone having a melting point of 77° - 78° C.

IR($\nu_{max}^{KBr}$ cm$^{-1}$) : 3250 (NH), 1755, 1720 (CO).

NMR(CDCl$_3$)δ : 2.76 - 3.66 (4H, m,

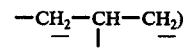

4.80 (1H, m,

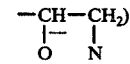

6.17(1H, broad s, NH), 6.9 - 7.4 (4H, m, aromatic protons).

MS(m/e) : 195 (M+).

Having now fully described the invention, it will be apparent to one of ordinary skill in the art that many changes and modifications can be made thereto without departing from the spirit or scope of the invention as set forth herein.

What we claim is:
1. 5-(o-Chlorobenzyl)-2-oxazolidone.
2. 5-(o-Bromobenzyl)-2-oxazolidone.
3. 5-(o-Fluorobenzyl)-2-oxazolidone.
4. 5-(o-Bromobenzyl)-2-oxazolidone.
5. 5-(m-Fluorobenzyl-2-oxazolidone.
6. 5-(o-Phenoxybenzyl)-2-oxazolidone.
7. 5-(p-Fluorobenzyl)-2-oxazolidone.
8. 5-(o-Methoxybenzyl)-2-oxazolidone.
9. 5-(p-Chlorobenzyl)-2-oxazolidone.

* * * * *

UNITED STATES PATENT AND TRADEMARK OFFICE
CERTIFICATE OF CORRECTION

PATENT NO. : 4,062,862
DATED : December 13, 1977
INVENTOR(S) : Yasuo Fujimoto et al It is certified that error appears in the above-identified patent and that said Letters Patent are hereby corrected as shown below:

IN THE CLAIMS:

Claim 4, delete "5-(o-Bromobenzyl)-2-oxazolidone." and insert

--5-(m-Bromobenzyl)-2-oxazolidone.--

Signed and Sealed this

Third Day of June 1980

[SEAL]

Attest:

SIDNEY A. DIAMOND

Attesting Officer     Commissioner of Patents and Trademarks